(12) United States Patent
Hall et al.

(10) Patent No.: US 6,419,708 B1
(45) Date of Patent: *Jul. 16, 2002

(54) CALCIUM-PHOSPHATE COATED IMPLANT ELEMENT

(75) Inventors: Jan Hall; Anatol Krozer, both of Göteborg; Peter Thomsen, Västra Frölunda, all of (SE)

(73) Assignee: Nobel Biocare AB, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/403,387

(22) PCT Filed: Apr. 29, 1998

(86) PCT No.: PCT/SE98/00787

§ 371 (c)(1), (2), (4) Date: Jan. 20, 2000

(87) PCT Pub. No.: WO98/48862

PCT Pub. Date: Nov. 5, 1998

(30) Foreign Application Priority Data

Apr. 30, 1997 (SE) .............................................. 9701647

(51) Int. Cl.$^7$ .................................................. A61F 2/28
(52) U.S. Cl. .................................. 623/23.57; 623/16.11
(58) Field of Search ........................... 623/16.11, 23.5, 623/23.53, 23.55, 23.57, 23.6

(56) References Cited

U.S. PATENT DOCUMENTS

| | | | |
|---|---|---|---|
| 4,330,891 A | | 5/1982 | Brånemark et al. |
| 4,965,088 A | * | 10/1990 | Shimamune et al. .......... 427/2 |
| 5,034,186 A | * | 7/1991 | Shimamune et al. .......... 419/9 |
| 5,205,921 A | * | 4/1993 | Shirkanzadeh .............. 205/318 |
| 5,258,044 A | * | 11/1993 | Lee ............................. 623/66 |
| 5,279,831 A | * | 1/1994 | Constantz et al. .......... 424/423 |
| 5,480,438 A | * | 1/1996 | Arima et al. ................... 623/16 |
| 5,897,592 A | * | 4/1999 | Caldarise et al .............. 623/16 |
| 5,947,893 A | * | 9/1999 | Agrawal et al. ............... 600/36 |
| 6,005,164 A | * | 12/1999 | Johansson et al. ............ 623/16 |
| 6,069,295 A | * | 5/2000 | Leitao .......................... 623/11 |
| 6,331,312 B1 | * | 12/2001 | Lee et al. .................... 424/426 |

FOREIGN PATENT DOCUMENTS

| | | |
|---|---|---|
| WO | WO 88/08460 | 11/1988 |
| WO | WO 94/25637 | 11/1994 |

OTHER PUBLICATIONS

US 6,117,172, 09/2000, Ripamonti et al. (withdrawn)*
Dijk, K. van et al., Influence of Annealing Temperature On RF Magnetron Sputtered Calcium Phosphate Coatings, *Biomaterials*, 1996, vol. 17, No. 4, pp. 405–410.
Wolke, J.G.C. et al., Study of the Surface Characteristics of Magnetron–Sputter Calcium Phosphate Coatings, *Journal of Biomedical Materials Research*, vol. 28, 1994, pp. 1477–1484.
Yamashita, Kimihiro et al., Bone–Like Apatite Coating of Alumina and Zirconia By RF–Magnetron Sputtering, *Phosphorus Research Bulletin*, vol. 6, 1996, pp. 123–126.

* cited by examiner

Primary Examiner—Paul J. Hirsch
Assistant Examiner—Michael B. Priddy
(74) Attorney, Agent, or Firm—Connolly Bove Lodge & Hutz

(57) ABSTRACT

The invention relates to an implant element for permanent anchorage in bone tissue in which at least the surface intended to face the tissue in the implantation region is made of a biocompatible material such as titanium and having a clinically well documented surface. The element is provided with a thin, uniform and adherent calcium-phosphate coating with a well controlled dissolution rate. The coating follows the topography of the underlying well documented surface in order to combine properties for rapid bone growth during the healing phase and properties for a guaranteed long-term stability during clinical loading conditions.

7 Claims, 21 Drawing Sheets

CALCIUM-PHOSPHATE COATED IMPLANT ELEMENT

BACKGROUND OF THE INVENTION

The invention relates to an implant element for permanent anchorage in bone tissue in which at least the surface intended to face the tissue in the implantation region is made of a biocompatible material such as titanium and having a clinically well documented surface.

It is previously well established to use medical implant elements for a variety of purposes. Specifically, in the dental field Brånemark System® implants for replacement of lost dental roots have been successfully used for 30 years. The treatment comprises three stages: (1) One or more titanium screws are installed in the jawbone and are left to integrate with the bone for between three and six months, (2) Special abutments are connected to the fixtures, (3) When the gums have healed, the dental prosthesis is fitted, for permanent use and providing a similar feeling as with natural teeth.

Titanium is a lightweight metal with high strength, low thermal conductivity and fine corrosion resistance. The most important property in this context is the unique biocompatibility of titanium which might be related to the spontaneous formation of titanium oxide on its surface. Brånemark System® is based on the ability of titanium to integrate permanently with bone tissue, which is a medical phenomenon named osseointegration.

The implant screws are machined from commercially pure titanium. The surface topography of the machined surface shows features in the micron range. According to U.S. Pat. No. 4,330,891 the interaction processes between the titanium oxide surface and the surrounding tissue which results in implant-bone integration are improved if the implant surface is micro-pitted with pits having a diameter in the range of from 10 nm up to about 1000 nm, i.e. the size of the micro-pitting approaches the order of magnitude of the cell diameter in the surrounding tissue or a few multiples thereof.

In addition to a well-defined implant surface topography special care also has to be taken with respect to the surgical technique to assure that the prerequisites for achieving osseointegration are fulfilled. The implant screws are normally installed in the bone tissue at a first operation. Thereafter they are left unloaded for a period of three to six months covered by the soft tissue. At a second surgical session the soft tissue covering the implant screws is removed and the screws are connected to a superstructure and loading can be permitted.

It is assumed that such a two-stage surgical procedure with an early post-operative period without loading is important for the implant stability during the early healing phase. However, the two-stage surgical technique is a disadvantage for the patient and makes the installation time-consuming and therefore expensive. It has also been demonstrated that for specific indications a correct clinical bone anchorage can be achieved using a non-submerged approach, i.e. a one-stage surgical procedure. Also in case of such a one-stage surgical procedure it is assumed that a critical healing period, approximately three months long, during which unfavourable loading should be avoided, is important in order not to jeopardize the process of osseointegration.

Specifically in the mandibular bone the success rate for this type of dental implants is very high. However, in the maxilla and the posterior mandible the success rate very much depend on the quality of the bone.

An object of the present invention is to provide an implant element which allows for a possible reduction of the healing period but which still guarantees a long term stability during clinical loading conditions.

A further object of this invention is to increase the possibilities to use the implants more successfully also in low bone qualities, which is often the case in the maxilla and the posterior mandible.

A review of the literature shows that implant mobility and radiographic bone loss are associated with failures; either to early (primary) failures or late (secondary) failures. The early failures are the consequence of biological processes which interfere with the healing process of bone and the establishment of osseointegration. The majority of these failures are host-related, whereas late failures are the consequence of mainly overload and host-related factors. Clinical retrieval studies indicate that a high degree of bone-implant contact is a consistent finding in functioning, successful clinical osseointegrated titanium implant systems (Sennerby et al, 1991). On the other hand, ongoing studies show that clinically mobile implants with radiolucency are characterized by absence of bone and the presence of fibrous capsule formation and inflammatory cells.

On the basis of available literature and knowledge it may therefore be concluded that the integration of titanium implants and bone and the maintenance of this integration are prerequisites for the clinically documented long-term function and relatively high success rate with this implant. However, experimental studies have shown that bone is not formed directly on the surface of the titanium implant. Instead the process of bone formation originates from existing bone surfaces and solitary islands of bone either in the bone marrow distant from the implant surface or in the distal threads. The bone formation is directed towards the titanium surface and the immediate interface zone is the last to be mineralized (Sennerby, Thomsen, Ericson, 1993a; 1993b). The early phase of bone healing is therefore of particular importance for the establishment of osseointegration. If the healing process is jeopardized, for instance by insufficient implant stability in bone of poor quality or other negative factors, such as previous irradiation of tissues or local inflammation, osteopenia and rheumatoid arthritis the implant-bone connection may be inadequate and the implant-bone structure may not withstand loading (Sennerby & Thomsen, 1993; Öhrnell et al, 1997, Brånemark et al, 1997). It is therefore an urgent need to improve the treatment of patients with the osseointegrated implant technique in case of non-optimal conditions. Such improvements may allow patients with a non-optimal, deranged and/or damaged tissue structure to benefit from treatment with osseointegrated implants.

It is previously known that coatings of biocompatible material of controlled chemical composition and crystalline structure may be deposited onto a substrate to provide articles to be used as medical, dental or orthopedic implants. An objective of such deposition or coating is to develop an implant with a surface which provides for a stable bone-implant connection.

An example of a suitable biocompatible material in this context is hydroxylapatite, i.e. $Ca_{10}(PO_4)_6(OH)_2$, and mixtures of calcium-phosphates, CaP, which resemble the primary inorganic chemical constituent of bone. Various attempts have been made to deposit CaP coatings onto metal substrates in which case the CaP mixture is acting as a biocompatible coating.

According to several scientific investigators, see for example Dhert 1992, CaP coatings may stimulate bone growth during an initial stage. However, the long term results are not convincing, see for instance Johnson B W et al (1992), Lemons J E et al (1988) and Gottlander & Albrektsson 1991.

A possible explanation for the poor long term results may be that the coatings which have been used so far normally have been plasma-sprayed to a thickness of 50–100 μm. Such coatings may have an inherent significant probability for fractures, which may be due to in vivo dissolution and the insufficient mechanical strength of the relatively thick coatings.

A review of the literature reveals that, in addition to the plasma spraying, there are several methods to prepare surface coatings. One way to classify these methods is to divide them into (1) those methods where a coating is prepared by "dry deposition" and (2) those methods where "wet" coating techniques are used.

The former methods include (i) plasma spraying, (ii) laser ablation, (iii) ion assisted sputtering and (iv) radio frequency (RF)-sputtering. The "wet" preparation techniques include: (i) dipping samples into a solution, (ii) electrolytically assisted CaP deposition and (iii) precipitation from supersaturated solutions.

None of these techniques is new per se; the principles underlying each method and the processing technologies used by each of them are in general well established and have been described in numerous publications, in particular with regard to formation of thin high $T_c$-superconducting films, optical coatings, hard film coatings etc. These methods will therefore not be described in any detail here.

In the following the different coating techniques will be discussed with respect to their advantages and drawbacks with respect to an implant element.

Plasma Spraying

Up to now plasma spraying (PS) has been by far the most commonly used method for producing CaP coatings. However, by this method only comparatively thick coatings have been produced, i.e. coatings having a thickness down to about 10 μm, but not thinner.

An object of our invention is to provide a substantially thinner CaP coating, since the probability for fractures will decrease with decreasing coat thickness. Therefore, the plasma spraying technique is not suitable.

Furthermore considerable amounts of impurities may be dispersed within the coating when the plasma spraying method is used in ambient air, for example an appreciable amount of carbonyls may be embedded in the CaP coating. Our invention describes an implant element which is prepared according to a well-controlled process without introduction of impurities.

Scanning Electron Micrograph (SEM) pictures of the surface morphology produced by a typical PS deposition technique shows a rough surface on at least 50 μm scale with a large variety of appearing structures. The surface structure which is obtained by the PS technique is dramatically different from the structure of the underlying substrate surface, for instance a titanium surface in case of a titaniun dental implant element.

Furthermore, it is usually necessary to have a rough underlying surface in order to obtain sufficient adhesion of the coating when using the PS technique. However, we can not allow for such surface roughening in the present invention since we wish to preserve the clinically well documented underlying surface.

Laser Ablation

Laser ablation is a relatively new deposition method that is able to produce a superior quality, comparatively thin high $T_c$ superconducting film coating. This method has also been used for depositing calcium-phosphate coatings.

It has been illustrated that the surface of a laser ablated film is rough on the micrometer scale with a broad diameter distribution of spherical particles. Thus, the coating does not follow the underlying substrate surface morphology.

Ion Beam Assisted Sputtering and Ion Beam Sputtering

These techniques may be suitable for use in research, but it is virtually impossible to implement them in any larger scale for production of CaP coatings. The methods are generally expensive due to the cost of the ion guns and they are also rather slow. A typical deposition velocity is approximately 4 nm/min for an ion beam assisted sputter deposited coating, see for instance JP-PS 2562283 (Ektessabi). The deposition velocity of ion beam sputtered coatings is typically an order of magnitude lower (approximately 0.4 nm/min).

Wet Chemical Coating Methods

The wet chemical coating methods, such as dipping of samples into a sol solution, precipitation from supersturated solutions and electrolytically assisted CaT deposition techniques, are powerful methods which are well suited for use in a large scale coating fabrication, and in principle it is possible to coat also substrates with a complex shape by means of these techniques. However, up to date, each of these wet methods suffers from specific drawbacks which have to be eliminated before they can be used routinely for calcium-phosphate coating.

Drawbacks with the wet chemical methods are the poor adhesion between the substrate and the coating, the low deposition velocity, difficulties to obtain films covering the entire substrate, that the apatite films consist of small sharp-edged crystallites, 2 μm–15 μm large and that the films do not appear coherent, but the grains seem to consist of piled crystallites.

Finally, it is extremely difficult to produce a coating which is free from contaminants stemming from the impurity ions dissolved in the solutions used, e.g. Mg, Si etc. It is virtually impossible not to modify the original surface stochiometry of the substrate by the simultaneous CaP adsorption of other ions from the solution. Thus in case of coating dissolution in vivo the substrate surface exposed will not be the one which is originally used or prepared, with regard to oxide composition and surface chemistry. It should be understood that such modification of the underlying surface is not acceptable according to our objectives as it might jeopardize the long term stability conditions for the implant device in question.

RF-sputtering

RF-sputtering techniques are previously described in, e.g.,

1. J. G. C. Wolke, K. van Dijk, H. G. Schaeken, K. de Groot and J. A. Jansen, "Study of the surface characteristics of magnetron-sputter calcium phosphate coatings", J. of Biomedical Materials Research, 28(1994) p. 1477,
2. K. van Dijk, H. G. Schaeken, J. G. C. Wolke, K. de Groot and J. A. Jansen, "Influence of discharge power level on the properties of hydroxyapatite-films deposited on Ti6A14V with RF magnetron sputtering", J. of Biomedical Materials Research, 29(1995) p. 269, and
3. K. van Dijk, H. G. Schaeken, J. G. C. Wolke and J. A. Jansen, "Influence of annealing temperature on RF magnetron sputtered calcium phosphate coatings", Biomaterials, 17(1996) p. 405.

These three references solely rely on physical vapour deposition. Nobel gas (Ar) is used for the RF-sputtering. When pure Ar-gas is used during the RF-sputtering process Ca/P values of approximately 2.05 (±0.15) are reported. This high Ca/P ratio is due to the fact that there occur preferential losses of e.g. POx and OH groups during the sputtering procedure (as well as during the plasma spraying and laser ablation techniques discussed above). Such losses result in high Ca/P ratios and negligible intensities of OH-vibrations in the FTIR spectra. Thus, using pure Ar-gas during the RF-sputtering process would give Ca/P values substantially higher than pure HA and the Ca/P ratio found in human bone, i.e. Ca/P=1.67. It should also be mentioned that the deposition velocities reported in the two first-mentioned references are 200 nm/min–250 nm/min.

The after-treatment of the coatings reported in ref.1 consists of an annealing "in air". In ref.3 a heating cell is used which is kept in a humid atmosphere. A decrease of Ca/P stochiometry upon heating from approximately 2.1 to 1.94 is reported at temperatures around 600° C.

In J. E. G. Hulshoff "Osteocapacity of calcium phosphate coatings", Thesis Catholic University Nijmegen, 1997, it is presented a coating preparation technique using RF magnetron sputtering where small amounts of water vapour or small amounts of oxygen were added to the argon (main gas carrier). However, the Ca/P ratios obtained by this coating preparation technique, see chapter 7 in Hulshoff et al, were also substantially higher than the Ca/P ratio found in human bone.

Furthermore, we note that the FTIR spectra from the coating produced by Hulshoff et al differs significantly from previously published FTIR spectra of typical calcium phosphates, as described by e.g. P. Ducheyne, W. van Raemdonck, J. C. Heughebaert and M. Heughebaert, "Structural analysis of hydroxyapatite coatings", Biomaterials, 7(1986) p.97, (see FIG. 7 in their article). The phosphate and hydroxyl bands, characteristic of typical calcium-phosphates and HA, seem to be absent in the FTIR spectra obtained from the coatings produced by Hulshoff et al. Specific combinations of CaP coatings with underlying substrate surfaces which would provide an optimal biological response was not presented by Hulshoff et al.

SUMMARY OF THE INVENTION

An object of the present invention is to provide a thin calcium phosphate coating on a clinically well documented implant element surface and which thereby combines properties for rapid bone growth during the early healing phase with the long term stability during clinical loading conditions for the well documented implant surface. Another object of the invention is to provide a comparatively thin coating which adheres well to the underlying implant surface, covers the surface as completely as possible and follows the implant surface morphology. A further object of the present invention is to provide a thin coating with a Ca/P ratio which is variable in a controlled manner. A desired crystallization of the coating would be achieved by a suitable after-treatment.

According to the invention a sputtering technique is used for providing a calcium-phosphate coating having a thickness from a few Ångström and more. Specifically, a RF-sputtering technique is used and the coating is chemically modified by mixing the Ar-gas with oxygen and hydrogen gases resulting in a preferred Ca/P ratio. An annealing after-treatment of the coated implant devices is performed in a specially designed flow cell at a high temperature.

BRIEF DESCRIPTION OF THE DRAWINGS

In the following a preferred embodiment of the invention will be more fully described with reference to the accompanying drawings in which.

DETAILED DESCRIPTION OF THE PREFERRED EMBODIMENTS

Figure 1:
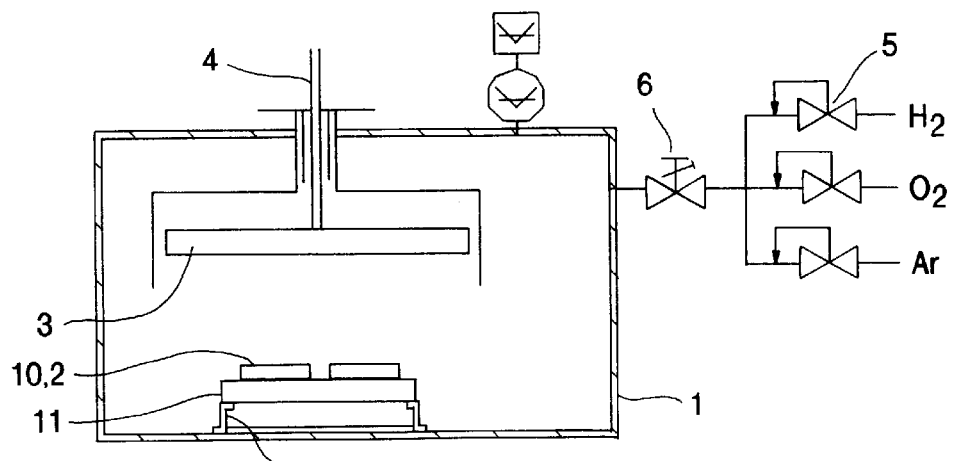
FIG. 1 is a schematic drawing of a deposition chamber used for the RF-sputtering technique.

In FIG. 1 it is schematically illustrated a deposition chamber 1 in which a number of samples 2 are prepared by reactive RF-sputtering.

The samples which are used are commercially available Brånemark System® titanium implant screws (fixtures) sold by Nobel Biocare AB. These implants are clinically well documented and made by machining commercially pure titanium. According to the invention a thin CaP coating is deposited on this well-documented implant surface for a conditioning of the surface in order to stimulate the bone-growth during the initial healing period.

According to the invention the thickness of the coating is in the range from a few Ångström and more. By means of the following examples it is demonstrated how such a thin coating adheres well to the underlying implant surface and covers the surface. The topographical properties of the underlying implant surface should not be affected by the coating. Since the coating is uniform and very thin, it will follow the underlying surface topography on a submicrometer scale. Thus, the clinically well documented surface topography is preserved with such a coating. The sputtering technique and the following heat treatment developed allows for a controlled variation of the crystallinity of the coating. Therefore, it is possible to control the rate of dissolution of the coating in vivo. After dissolution of the coating the originally clinically well documented surface should be maintained. As soon as the coating has made its contribution to a more rapid bone growth it is dissolved and the originally clinically well documented surface is exposed to the surrounding bone tissue.

The composition of the calcium-phosphate coating has a Ca/P ratio which is close to stochiometric HA and the Ca/P ratio found in human bone. Such a Ca/P ratio may allow for optimal interaction between the coating and the surrounding tissue. It should be understood that HA is a complicated compound with a chemical unit formula containing 22 different atoms. There exist at least 12 related calcium phosphates differing from HA by the different Ca/P atomic ratios ranging from 2—tetracalcium phosphate, 1.67—hydroxyapatite, and to 0.5—calcium metaphosphate. In addition many of the apatites can be synthesized in different crystallographic structures. The conditions at which HA is formed are often close enough to the formation conditions of other apatites and, as a result, a film that is formed may contain a mixture of various proportions of different apatites.

Two further aspects that influence the functional performance of a coating should be mentioned here before the sputtering technique for providing the desired coating is described, namely the morphology of the deposited CaP film coating and the crystallographic structure of the film. Both depend on the deposition technique chosen, but to some extent they can be modified by after-treatment. According to our invention the coating may be crystallized by means of an after-treatment at a temperature of 600° C. under humid atmosphere, see below.

The surface morphology and roughness down to about 200 nm scale can be studied by using Scanning Electron Microscopy while the studies of the atomic scale morphology are usually performed by using Atomic Force Microscopy. Qualitatively the structure of a thin film can be established by using X-ray diffraction techniques, but the Transmission Electron Microscopy can also be used. The latter technique requires a substantial amount of additional sample preparation which may induce artificial modifications to a coating.

The RF-sputtering illustrated in FIG. 1 is performed at a base pressure of approximately $10^{-6}$ torr and at a process pressure of approximately $10^{-3}$ torr. As a target a plasma sprayed 3 mm thick HA coated Cu-holder plate 3 is used. The target 3 is mounted on a water cooled target holder 4. The deposition chamber as well as the target holder devices are commercially available per se and will not be described in any detail here.

Oxygen, hydrogen and argon gases were used during the reactive sputter deposition and connected to the chamber 1 via pressure regulators 5 and a shut-off valve 6 as indicated on the drawing. Gas composition, gas pressure and gas flow could all be varied independently from each other during the deposition process. The total power (power density) applied to the target could also be varied from approximately 100 W (0.55 W/cm$^2$) to about 600 W (3.3 W/cm$^2$).

Figure 2:
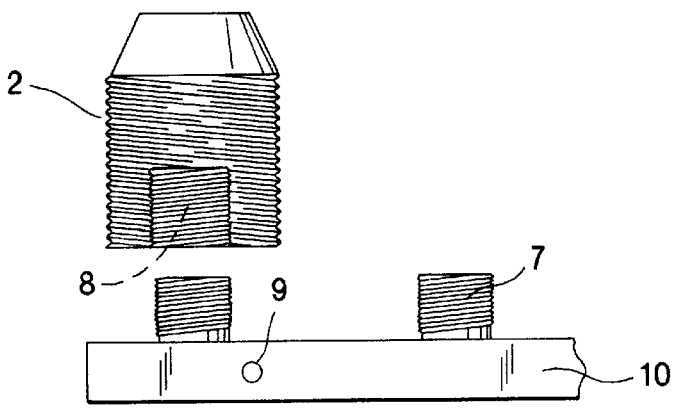
FIG. 2 is a schematic drawing of a mounting for the samples.
Figure 2:

The samples 2 were placed on an electrically grounded plate 12 located approximately 50 mm away from the target 3. The mounting of the samples in the form of titanium fixtures are schematically illustrated in FIG. 2. Each fixture (implant screw) was attached to a screw holder 7 by the internal thread 8 in the upper section of the screw. There was place for ten screws in a line in each holder 10. Each holder 10 has two spikes 9 on its side, i.e. for rotation by 90° with respect to the implant screw axes. Five implant screw holders 10 could be mounted onto a special platelet 11 provided with two holes matching the spikes 9 on the screw holders. Thus at each deposition the threaded portion of 50 implant screws was in the line of sights for the sputtered material. To cover the entire threaded area each screw should be turned by 90° four times during the deposition or an automatic rotation facility could be used.

The film thicknesses that can be produced by means of this RF-sputtering technique are limited only by practical considerations with respect to the length of the deposition time. In our examples we have an upper thickness limit of 3 μm, but it is possible to deposit thicker films if required (up to 10 μm). The method allows to deposit films down to a few Ångströms. In our examples we have a lower thickness limit of 0.1 μm (100 nm).

It was found that the composition of a coating depended mainly on the gas deposition parameters used, and varied only slightly with the power density applied to the target 3. For example if only Ar was used as a carrier gas during the deposition process, the Ca/P ratio of the coating was higher than 2 in agreement with the previously reported results from Jansen et al. This Ca/P value remained approximately constant independent from the power delivered to the target. Admixing oxygen into the carrier gas flow reduced the Ca/P ratio until it reached a value of approximately 1.68 (±0.05), i.e. close to a stochiometric HA. This value remained constant for oxygen to argon flow ratios between 10% and 40% of the total gas flow ($O_2$ flow between 5 ml/min to 20 ml/min admixed with 50 ml/min Ar). Admixing additional hydrogen flow to oxygen argon mixtures ($H_2$ flow between 5 ml/min to 20 ml/min) did not produce noticeable differencies in the Ca/P composition, but did change the FTIR spectra.

For a given gas composition and flow the total gas pressure in the sputter chamber 1 produced only minor changes in the stochiometry of the coating. The general tendency was that an increasing total pressure at a given flow increased the Ca/P ratio.

Although the film composition was weakly dependent on the power applied to the target 3, the deposition velocity varied with the power stronger than linearly. A power of 400 W was therefore applied to the target during the deposition process. The deposition time for forming a 0.2 μm thick film coating then took approximately 30 min at the pressure(s) used.

It has been observed previously by Jansen et al. that the coatings produced by RF-sputtering were amorphous, i.e. they either did not produce a well resolved diffraction peaks in X-ray experiments, or the diffracted peaks were superimposed with a characteristic "slopy" background. To crystallize the deposited films a treatment has to be performed after the deposition process. A conventional treatment consists of heating the samples in air to temperatures of up to 1000° C. However, heating in air introduces, an appreciable amount of impurities into the bulk, mainly various C—O compounds. Use of such high temperatures often results in a partial peeling off of the films.

Figure 3:
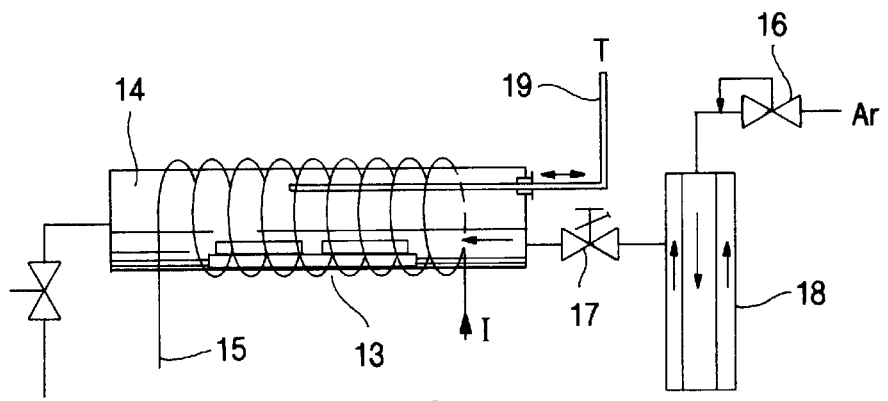
FIG. 3 is a schematic drawing of a special heating reactor for an annealing after-treatment of the coated implants.

A special heating reactor 13 has therefore been constructed in order to anneal the samples in our case, see FIG. 3. The reactor consists of a 500 mm long quartz tube 14 with a heater spiral 15 wrapped around it as shown in the figure. The quartz tube is connected to the gas supply in the form of an Ar—$H_2O$ mixture via a pressure regulator 16 and a shut-off valve 17. A flow controller and gas humidifier 18 are connected between the pressure regulator and the shut-off valve. The back-streaming of the gas from the ambient is reduced by slightly overpressuring the reactor and allowing a length of at least 400 mm behind the second shut-off valve. The cell is heated from the outside and the temperature is measured and regulated by a stainless steel-encapsulated thermocouple 19 which is movable inside and along the axis of the quartz tube. This allows for determination of the temperature distribution along the heated part of the reactor. Up to 40 samples (4 screw holders carrying a maximum of 10 screws each) can be heated simultaneously with maximal temperature variations of ±10° C.

The crystallization of amorphous matters can often be divided into three stages: (i) the initial stage when stable crystallite nuclei are formed, (ii) the growth of non-overlapping crystallites and (iii) finally the growth of overlapping crystallites (Orowan ripening). There are two important parameters that are governing all the three stages and which can be externally selected: the temperature of the sample and the total time during which the sample is heated. In the first stage it is the temperature and the balance of the free energy difference between the crystalline vs. the amorphous state of the material that govern the critical size for nuclei stability and their density. At higher temperatures fewer stable nuclei are formed and therefore the onset of stage (iii), i.e. the overlapping of nuclei, occurs at a larger average grain size compared with lower temperatures. Also, it is usually observed during stage (ii) that the diffusional growth rate of stable nuclei increases with increasing temperature. At a given temperature on the other hand, the longer the heating time the larger is the recrystallized volume. If stage (iii) is reached, the further growth of nuclei occurs by "swallowing" of grains by other larger grains because of impingement, and the average grain size therefore increases.

By means of visual observation it has been found that for temperatures higher then 650° C. the samples became discolored, and for some of the samples the coating peeled off from the titanium substrates. These findings then were in agreement with the findings of Jansen et al. Therefore, all the crystallizations have been performed at a temperature of 600° C. in our case.

The X-ray diffraction of the samples heated to a temperature of 600° C. for different time intervals showed that the total intensity of the diffracted X-rays increased with time in the time interval of 0.5 h–6 h after which the increase in intensity levelled off. Thus it is possible to vary the crystallinity of the coating and therefore its dissolution properties in vivo by varying the time for heat treatment with constant temperature.

In the following some examples of preparations will be described with reference to the graphs illustrated in FIGS. 4–17. In these examples the XRD spectra were obtained for samples prepared using different deposition conditions with respect to gas composition and subject to different heat treatments after the deposition.

The experimental conditions at which each of the samples presented in the subsequent figures was prepared are given within each figure. The following sample conditions will be described:

(i) deposition in pure Ar;

(ii) deposition in pure Ar and subsequent heat treat ment;

(iii) deposition using mixtures of Ar and oxygen during RF-sputtering with oxygen ranging from 5% of total gas flow to 30% of total gas flow;

(iv) subsequent heat treatment of each of the samples;

(v) samples deposited in a mixed flow of oxygen, hydrogen and Ar (12% $H_2$, 25% $O_2$);

(vi) heat treatment of these samples;

EXAMPLE 1

Figure 4:
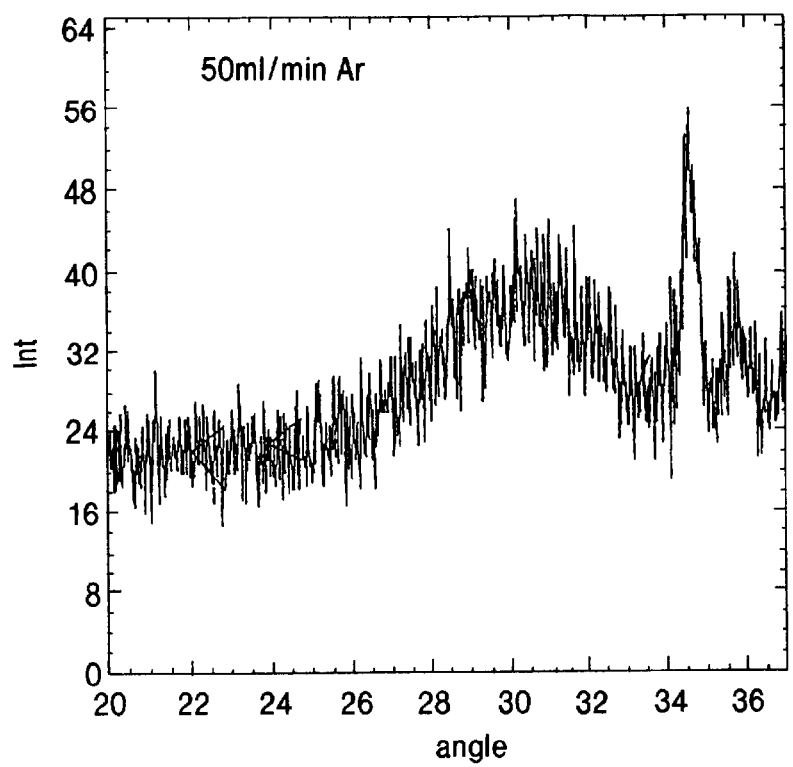
FIGS. 4–17 are graphs of different surface preparations characterized by means of X-ray diffraction (XRD) technique.

The graph in FIG. 4 represents samples deposited in pure Ar. The Ca/P ratio was approximately 2. The X-ray spectra of the untreated samples were characteristic of amorphous material with a broad feature around 30° with FWHM extending over a wide range of angles.

EXAMPLE 2

Figure 5:
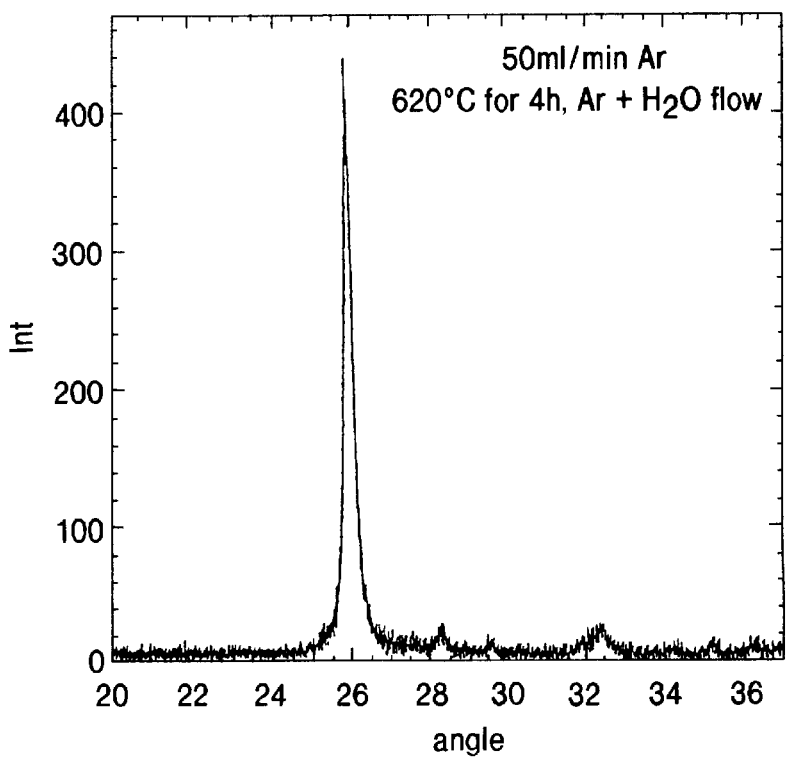
Figure 6:
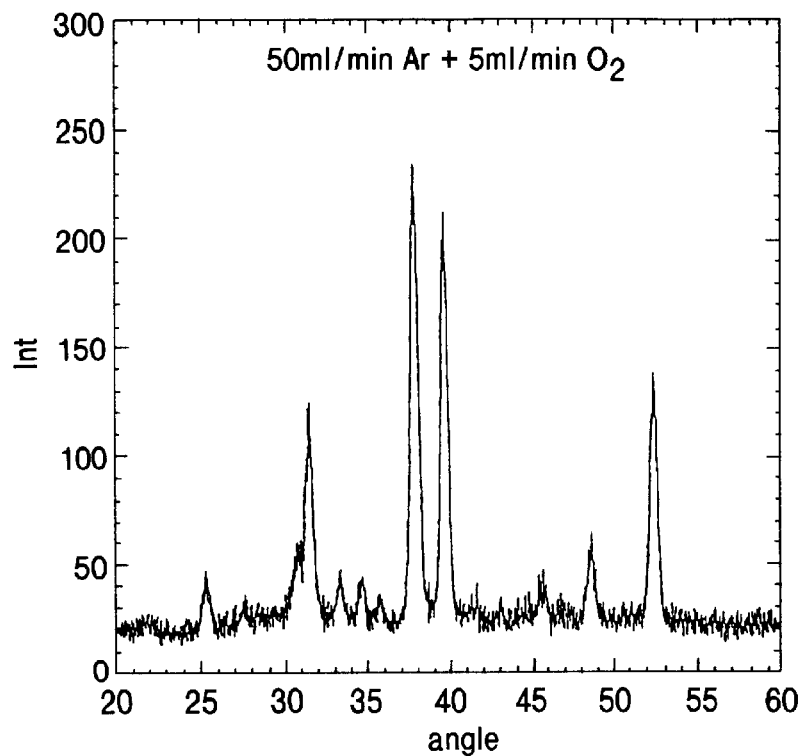

The graph in FIG. 5 represents samples deposited in pure Ar and annealed in Ar+$H_2O$ at 600° C. for 4 h. XRD show that samples crystallized preferentially with a (002) reflection peak when the samples were annealed in a humid atmosphere. According to both XPS and RBS (see below) the Ca/P ratio for the samples remained high, and in addition the heat treatment introduced large and long ranged concentration gradients (according to RBS).

EXAMPLE 3

The graphs in FIGS. 6–11 represents samples deposited in a mixture of Ar and oxygen with oxygen ranging from 5% of total gas flow to 30% of total gas flow. Although there was no indication of grain structure in the scanning electron microscope investigation of the samples (see FIG. 24 below) down to grain sizes well below 100 nm, the XRD on the prepared samples did show diffraction peaks that differed for different sputter conditions. Although most of the peaks could be assigned to HA a closer inspection showed that both samples deposited in 5% oxygen flow and in 20% oxygen flow contained some TCP. It is virtually impossible to give an estimate of the amount of TCP in these samples because quantification of XRD spectra from foils or thin films is in general not possible. Evaluating the intensity ratios of peaks that can be assigned to TCP and to the HA in FIGS. 7 and 11 will only give an upper ratio on the TCP content of approximately 15% and 30% for the samples shown in FIGS. 7 and 11, respectively. The samples prepared using 15% of oxygen in Ar contained less than 10% of TCP using the same evaluation procedure. The only distinguishable TCP reflection seen in all these samples was one at 31.5°.

EXAMPLE 4

Figure 16:
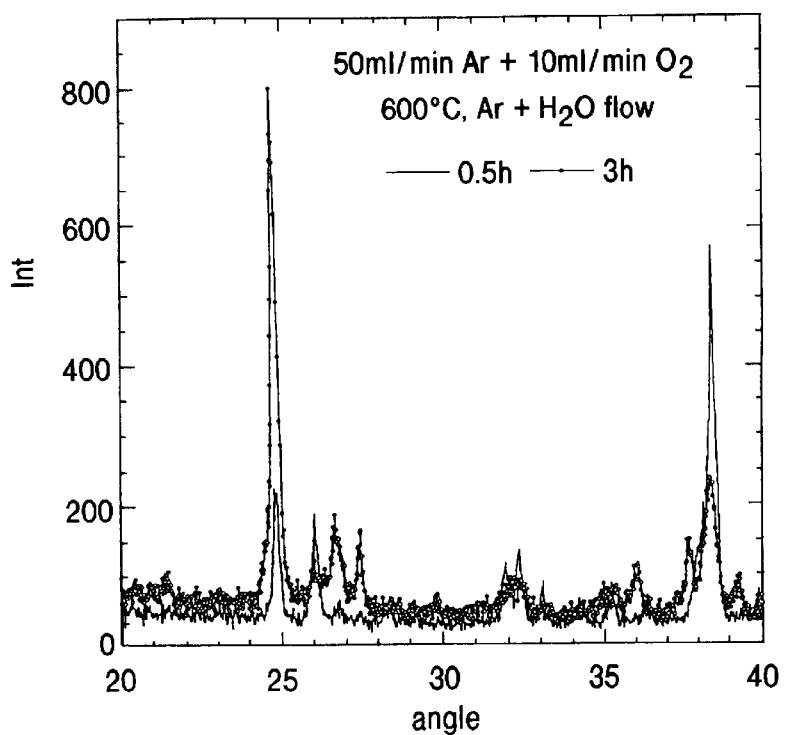
Figure 17:
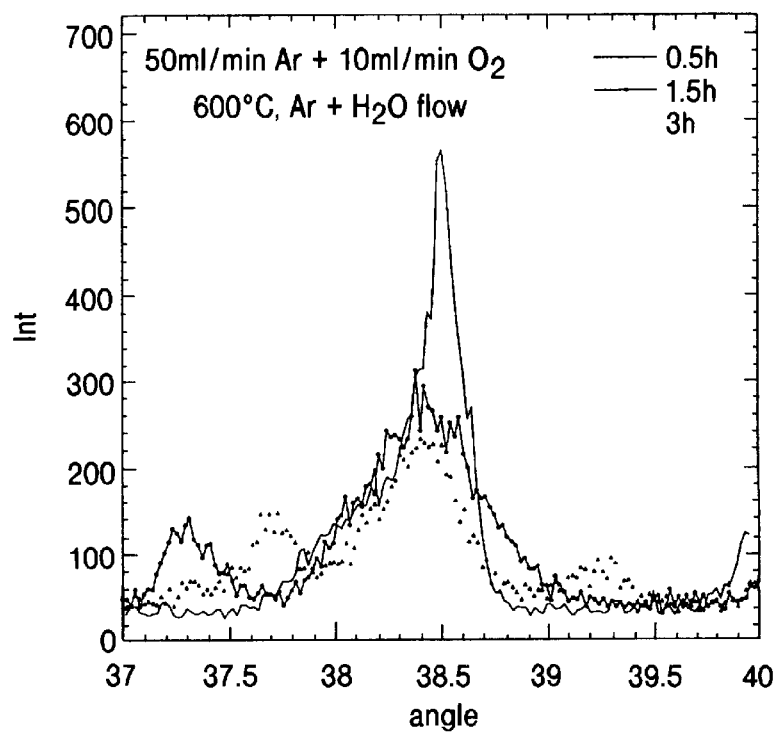

The graphs in FIGS. 16–17 represent samples deposited under the same conditions as in examples 3 but with varying time intervals for a subsequent heat treatment of each of the samples. Apart from further crystallization different heat treatment procedures resulted in somewhat different textures of the samples. The main changes could be described by the changes in the relation between the intensity of the (002) reflection compared to the intensity of other peaks in the spectra. Contrary to the case of pulverized HA (standard sample for XRD measurements) the intensity of the (002) reflection was dominant for the films obtained in Ar—$O_2$ mixtures. Actually, it carried more than 50% of the total spectral weight for all of the heat treated samples prepared using Ar—$O_2$ mixtures.

Note the decrease in the intensity of the reflections due to Ti substrate with increased heating time as shown in FIG. 17. The decrease of the substrate signal is due to the fact that the degree of crystallinity of the coating increases and causes a larger portion of the X-ray intensity to be channeled by the reflections from the coating.

EXAMPLE 5

Figure 12:
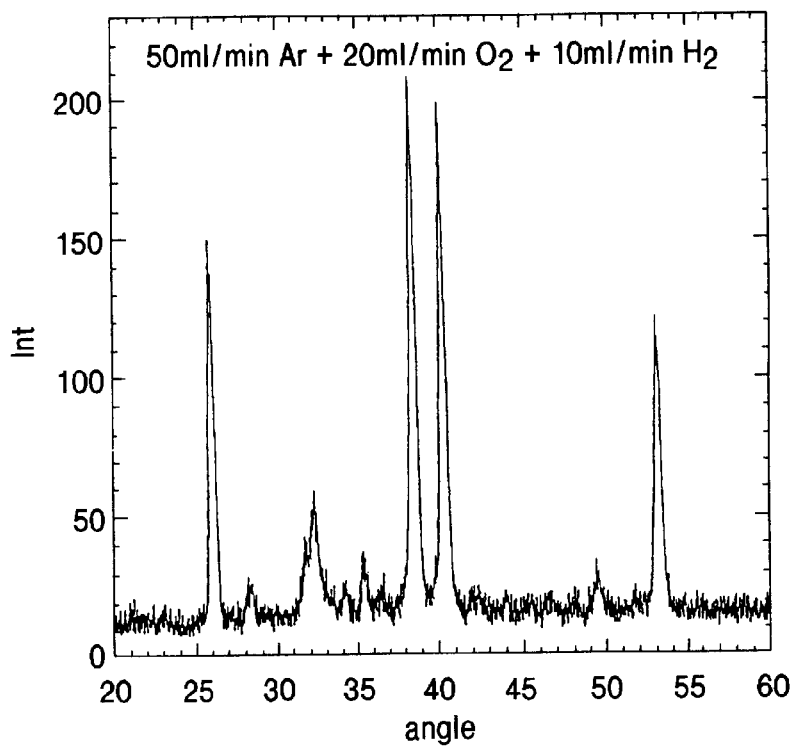
Figure 13:
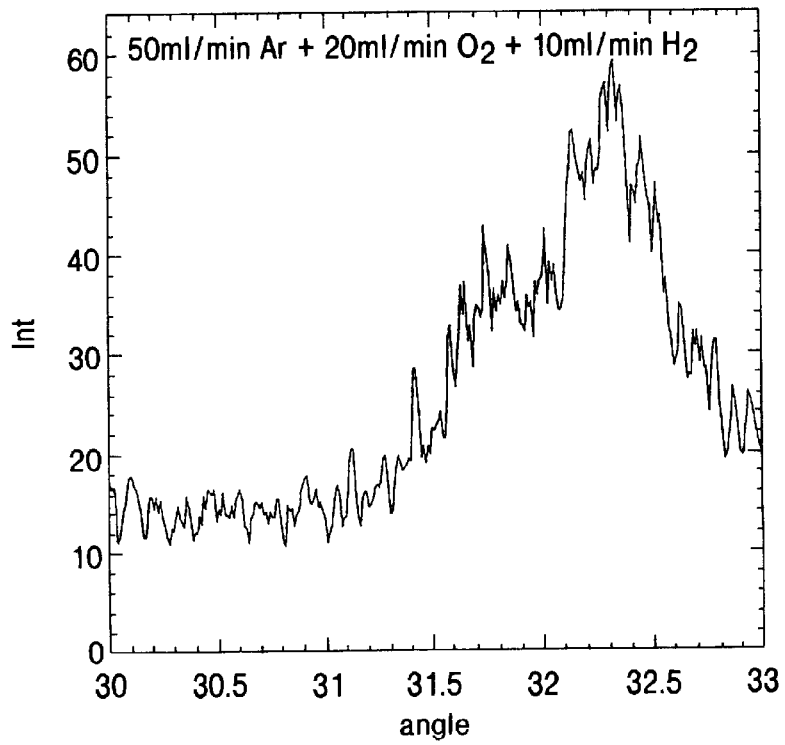

The graphs illustrated in FIGS. 12 and 13 represent samples deposited in a mixed flow of oxygen, hydrogen and Ar. The samples prepared by these mixtures differed somewhat from the samples prepared without hydrogen as can be seen in the figures.

EXAMPLE 6

Figure 14:
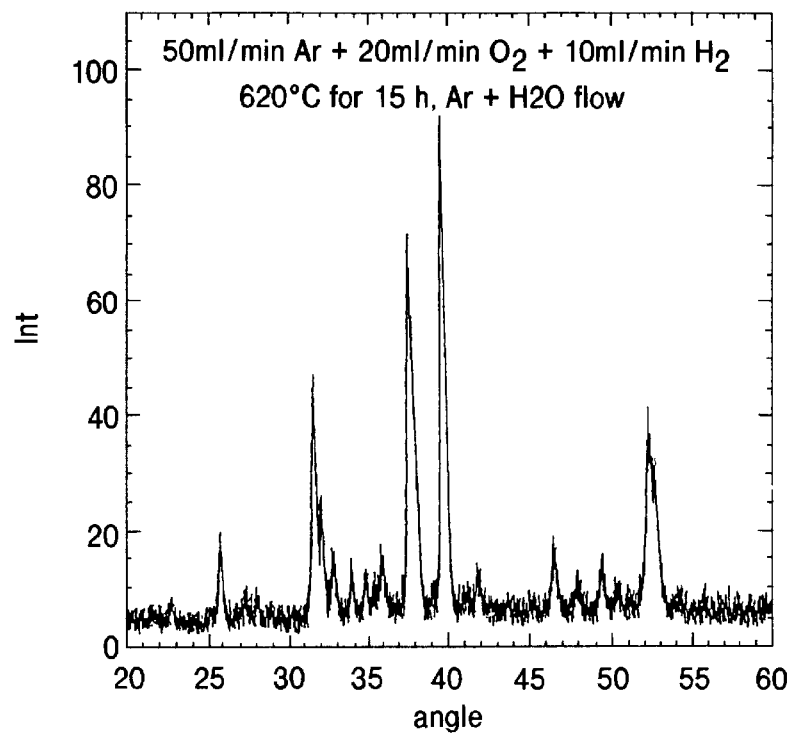
Figure 15:
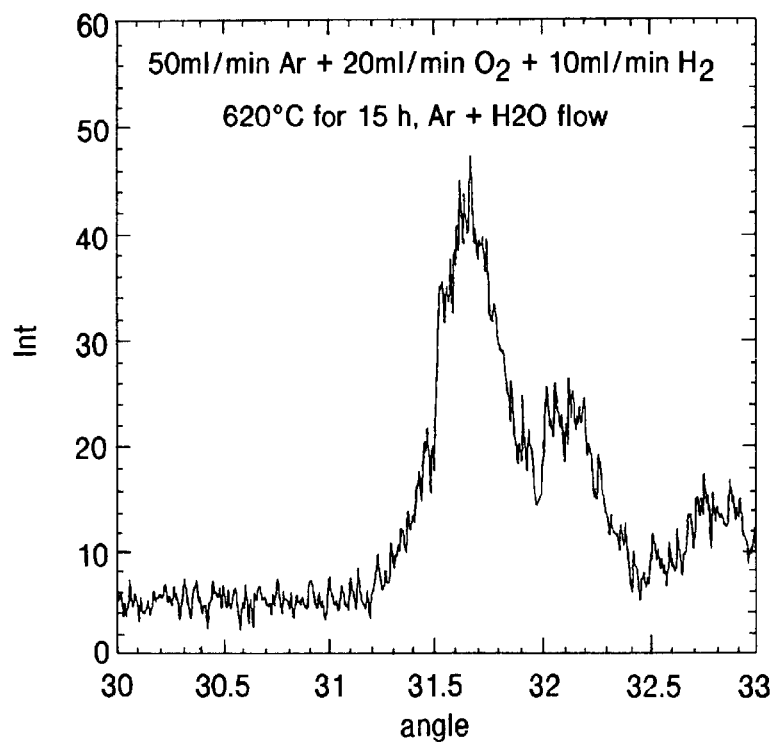

The graphs illustrated in FIGS. 14 and 15 represent samples deposited under the same conditions as in example 5 but with a subsequent heat treatment in Ar+$H_2O$ flow at 620° C. for 15 h. After heat treatment the intensity ratios of various spectral features resembled more the intensities observed in the stochiometric pulverized HA standards than did the intensities of the previously described samples. Thus the relative intensity of the (002) reflection, although still dominant in the untreated samples, decreased with the heat treatment, while the intensity of the reflections around 32° increased. The possible TCP content of the untreated samples was lower then in all of the previously described samples, i.e. the samples prepared without hydrogen. Again, the only possible non-HA reflection was the TCP-reflection seen in these samples at the 31.5°. The TCP content of the heat treated samples was lower then that for the samples prepared without hydrogen admixture.

Heat treatment clearly increased the degree of crystallinity of the samples. Quantitatively the degree of crystallization cannot be assessed from the XRD spectra since the spectra from thin films are not amenable to quantitative analysis. Qualitatively however, the XRD results shown in FIGS. 16 and 17 show clearly the growth of the diffracted peaks for a sample heated for 1.5 h. Further heating (for 3 h) resulted in only minor (mainly crystallographic, change of texture) changes of the spectral intensity. FIG. 16 shows the increase of the dominating (002) HA reflection peak upon prolonging the heat treatment. In FIG. 17 it is seen that the spectral weight of Ti reflections decreases with the heating time, but the main changes occurs during the first hour(s) of heating. This observation has been further corroborated by two additional observations, namely by the scanning electron microscopy (SEM) experiments and by the dissolution experiments performed on the untreated and on the heat treated samples.

We have therefore concluded that heating at a temperature of 600° C. for 15 h was sufficient to produce full crystallization of the films, and that the only result of further treatment (if any) would possibly produce increased grain sizes within the films.

In addition to the described XRD surface characterizations, characterizatins of the Ca/P ratio have been performed by using two different methods: Rutherford backscattering (RBS) and X-ray photoemission spectroscopy (XPS or ESCA) together with ion sputter profiling, see FIGS. 18–23. Each method is well established and will not be described here in any detail.

RBS gives information on sample composition throughout the thickness of the sample. The depth resolution depends among other parameters on the probed depth and is typically larger than 20 nm and the compositional sensitivity is below 1 at %. However, the compositional information that can be obtained without use of spectra from standard samples is reliable to within 5%. ESCA combined with ion depth profiling can give compositional information with a monolayer resolution, but since various artifacts can arise during ion sputter removal of the coating (especially preferential sputtering) the results obtained with this method were cross checked by, e.g., RBS. Other issues that RBS is unable to give answers to are surface impurities and light element content of the sample such as carbon and hydrogen.

Figure 18:
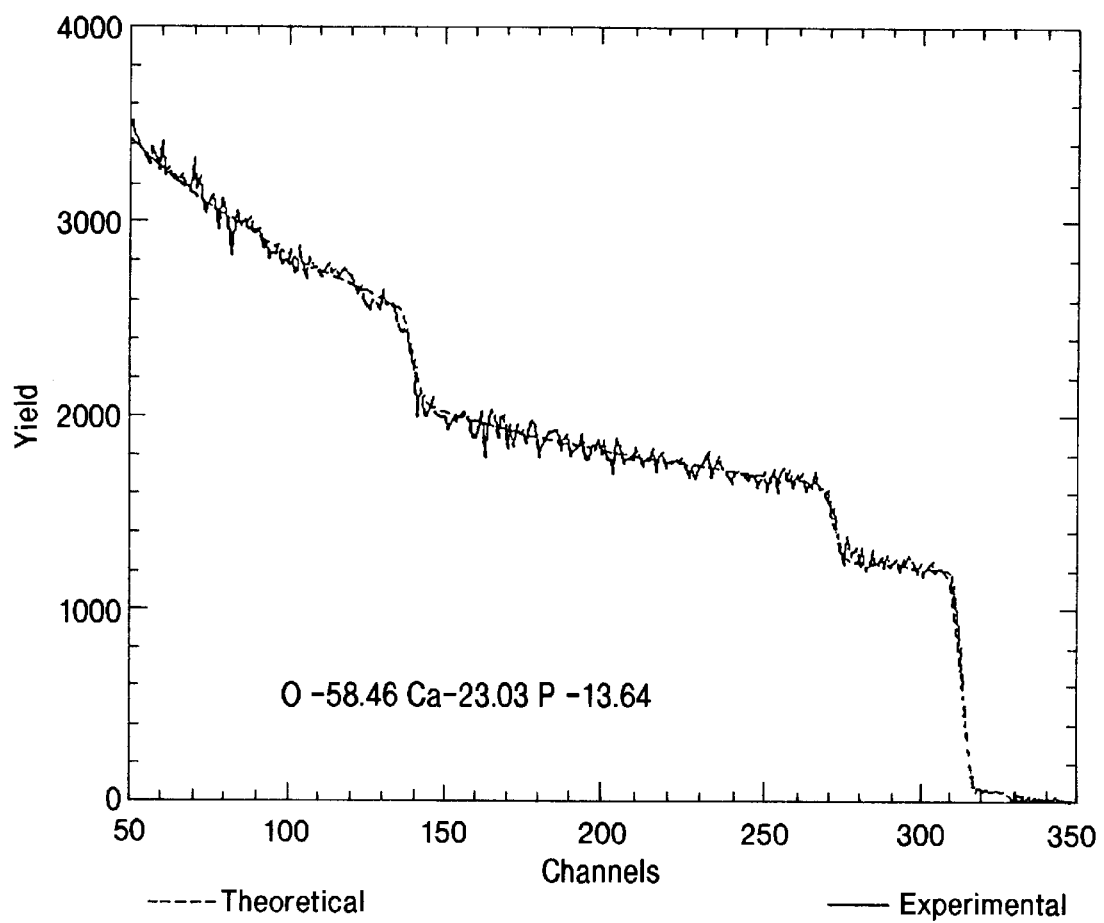
FIGS. 18–32 are graphs of different surface preparations characterized by means of Rutherford backscattering (RBS) technique and X-ray photoemission spectroscopy (XPS or ESCA) technique together with ion sputtering profiling, SEM pictures and FTIR technique.

FIG. 18 shows a typical RBS spectrum obtained on a sample deposited in a mixed flow of (20 ml/min) oxygen/(10 ml/min) hydrogen/(50 ml/min) argon. Along with experimental data (dots) the figure also shows the theoretical fit to the data (solid line) from which the composition of the sample can be calculated. The Ca/P ratio for this particular coating is 1.69, and the chemical formula for this coating is close to $Ca_5(PO_4)_3(OH)_{0.7}$. As can be seen from the RBS data the composition of the sample is uniform throughout its thickness, at least within the limits of the sensitivity of the method. If the sample would have compositional gradients, than the experimental data would exhibit additional sloping as a function of energy loss (channel number) and it would not be possible to fit the data throughout the whole energy range characteristic of a given peak (for example the gradient in calcium would appear as additional sloping starting approximately from channel 310 and continuing to approximately channel 270, where it would be superimposed on the ions scattering off P).

It can also be seen that the coating shown in FIG. 18 is thick enough to completely suppress ion backscattering from the titanium substrate. By producing coating of different thickness in a range where Ti is visible it was possible to cross check the coat thickness obtained by using stylus profilometry with RBS, and also to calibrate the sputtering rate of the coating using ion bombardment (see the ESCA method below).

XPS technique was used to elucidate the surface and the Ca/P ratio characterization of the coatings using compositional analysis of the spectra.

Figure 19:
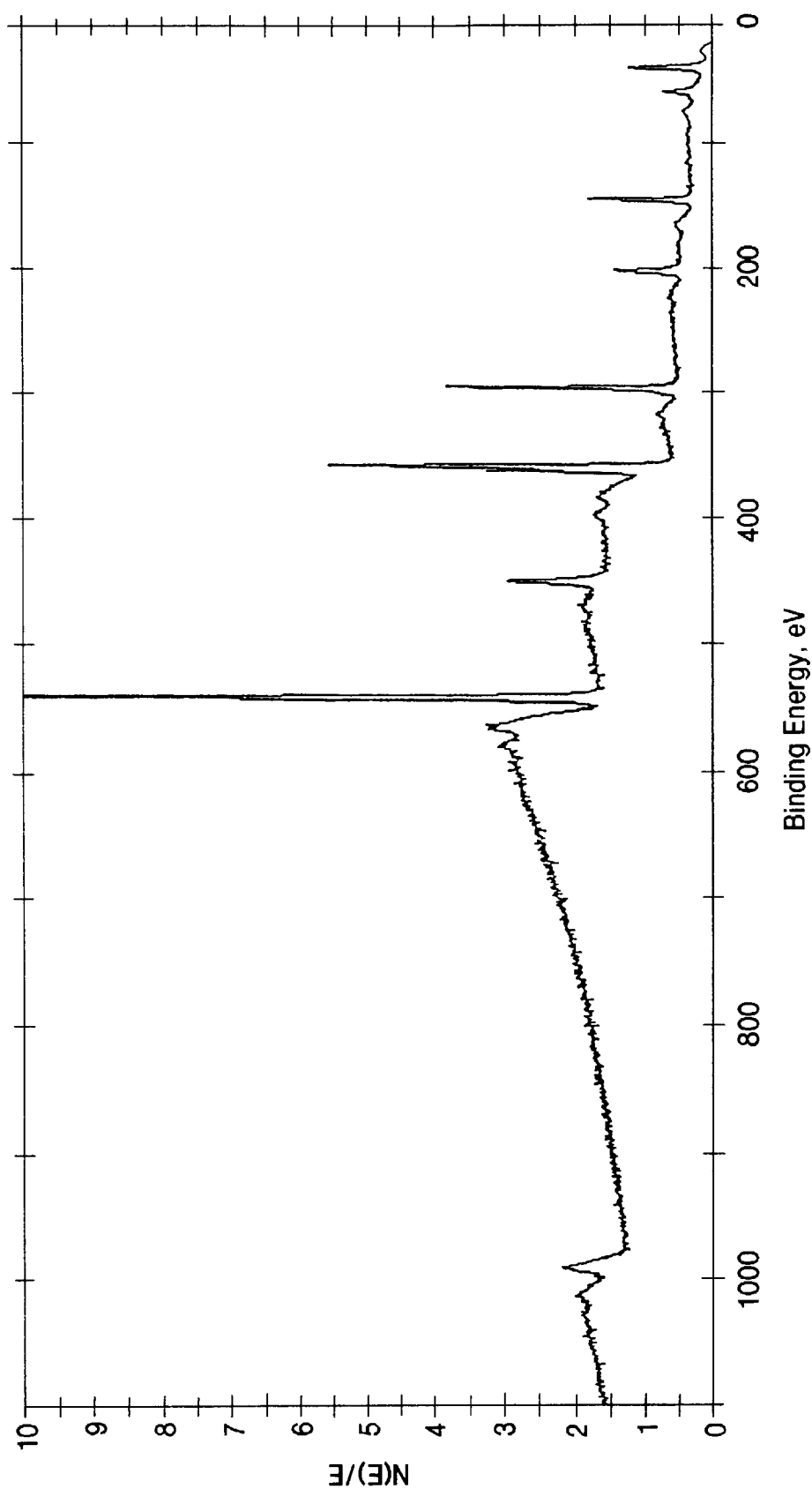

FIG. 19 showed a typical spectrum of as deposited approximately 3 μm thick calcium-phosphate coating deposited using the same conditions as the coating shown in FIG. 18. As can be seen from the figure the main impurity on the surfaces of as deposited coatings was always carbon. The carbon contamination varied between 25 at %–35 at % and depended mainly on handling of the coated surfaces. A careful compositional analysis of the spectra of coatings deposited at different times and using different deposition parameters revealed traces of other impurities, mainly of Si, S and Cl—about 1 at %. As can be deducted from the compositional analysis of the spectra in FIG. 19 the Ca/P ratio at the surface was approximately 1.4.

Figure 20:
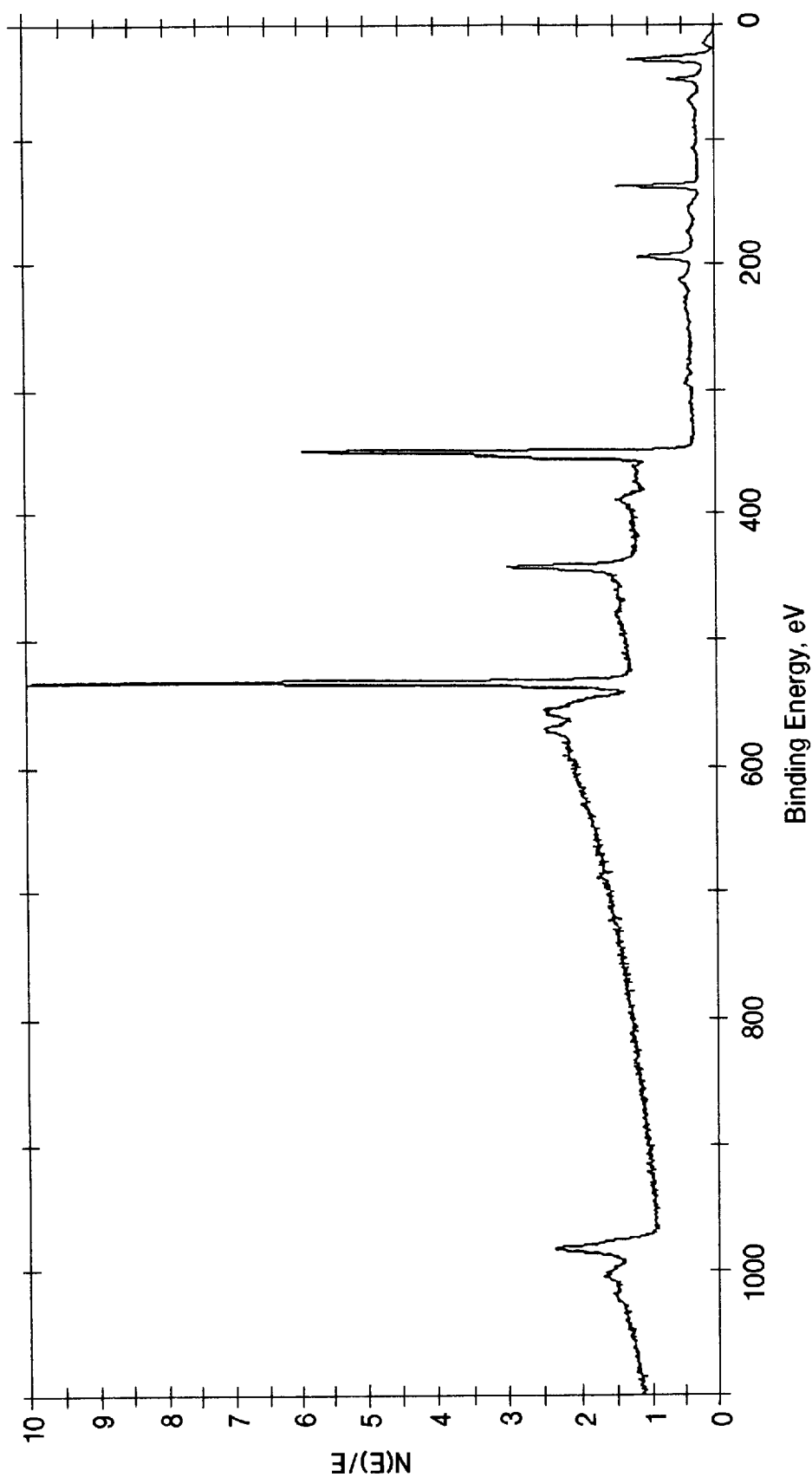

The carbon contamination on the surface could be easily removed by irradiating samples with UV produced ozone. This is illustrated in FIG. 20 which shows the spectra for the sample characterized in FIG. 19, but after 0.5 h of irradiation with the ozone. The elemental analysis shows that carbon constitutes less than 4 at% of the surface composition. The Ca/P ratio increased on this almost carbon-free surface to 1.66. This suggests that either carbon predominantly binds at or close to Ca sites and thus obstructs the signal from Ca, or phosphorus is partly removed by ozone. We believe that the former possibility is the most probable one.

We have controlled that the almost carbon-clean calcium-phosphate surface remained reasonably clean for at least 10 min in air, and therefore used the ozone cleaning before the in-vivo use of implants.

The carbon contamination increased somewhat during heat aftertreatment, and some carbon containing species diffused into the bulk. However, the amount of carbon in the bulk as determined using sputter ion depth profiling never exceeded 5 at %.

Figure 21:
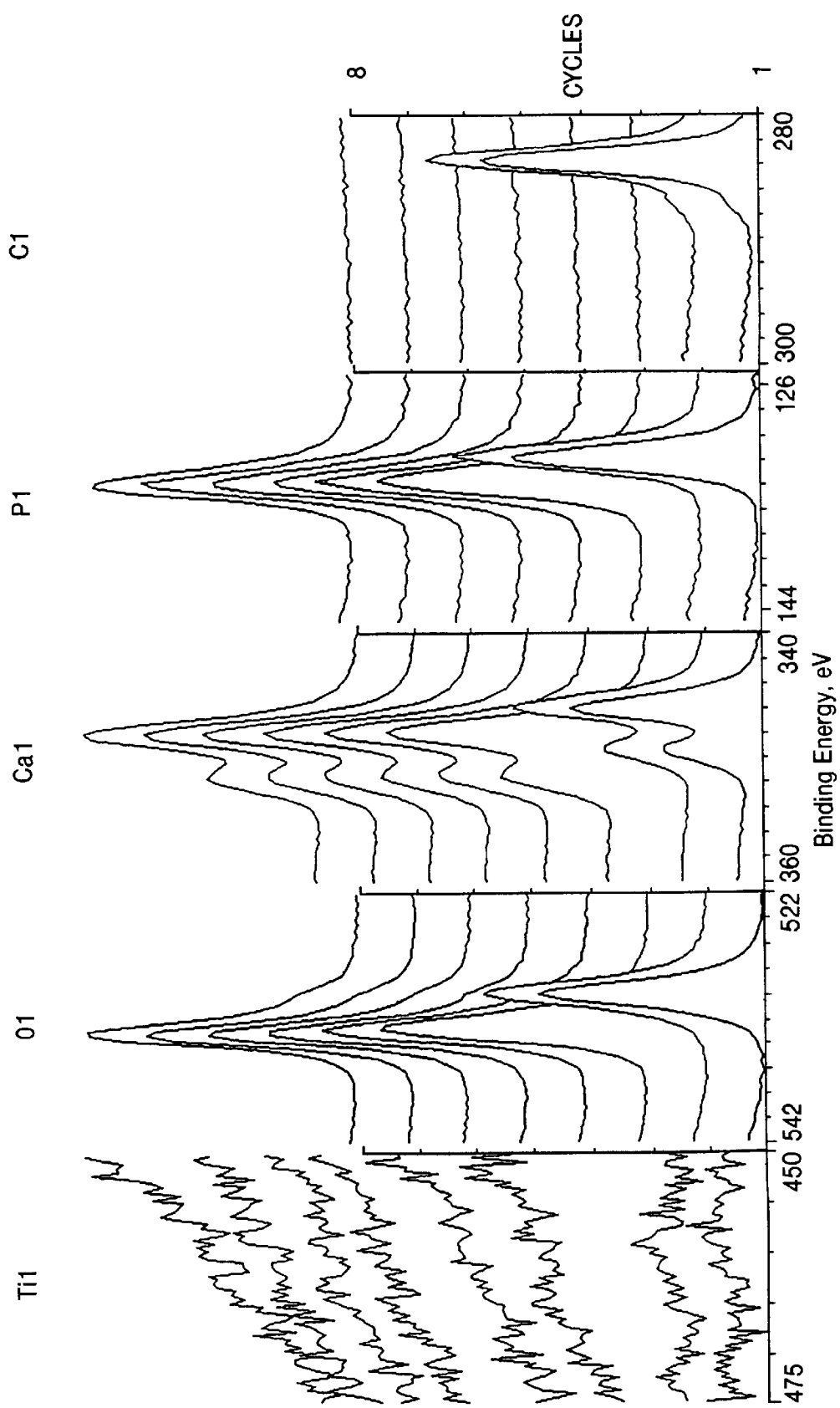
Figure 22:
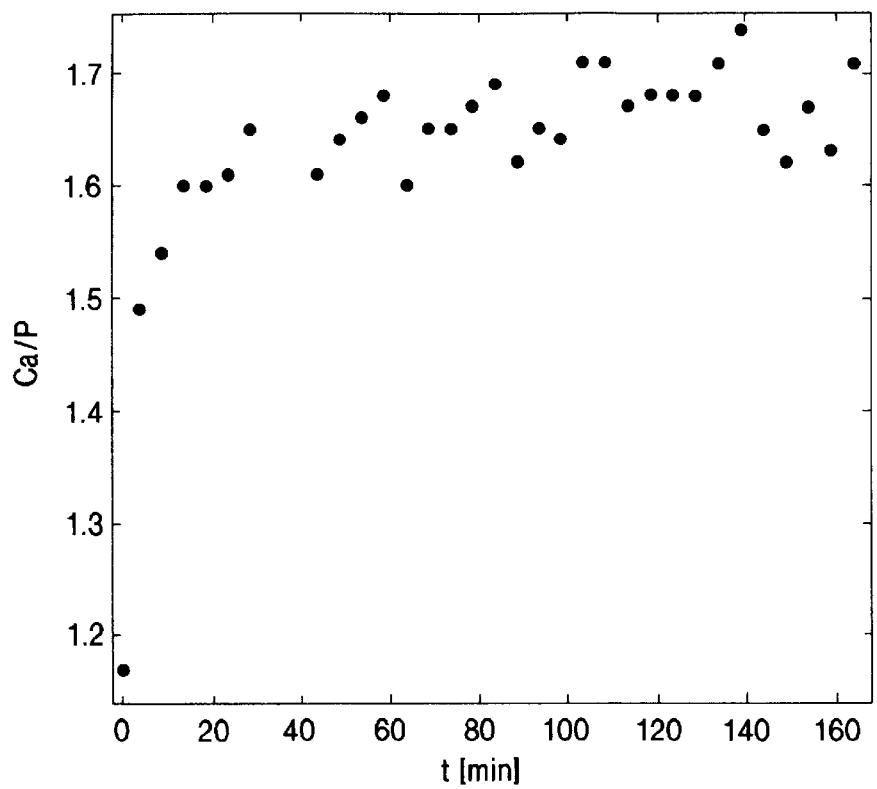

To investigate the Ca/P ratio in the bulk of the film we have collected ESCA spectra after subsequent time intervals (either 2 min or 5 min) during which the film under investigation has been bombarded by Ar-ions. ESCA spectra were collected over energy intervals of: O 1s, Ca 2p, P 2p, C 1s and Ti 2p peaks. An example of such depth profile spectra is shown in FIG. 21. The compositional analysis of these spectra with regard to the Ca/P ratio illustrates a typical composition profile vs. depth of the coating and is shown in FIG. 22. After an initial increase due to the above mentioned carbon surface contamination (this particular sample was not subject to ozone treatment) the Ca/P ratio remains constant at approximately 1.65 (±0.07). This was typical of all samples prepared by us, also of the ones which underwent an after-treatment. Note that the Ca/P ratio stabilizes only after sputtering for approximately 10 min. This effect is partly due to the smearing of the surface carbon contamination within a few nm inside the coating by bombarding ions, but can also arise if one of the species is sputtered preferentially by the argon ions. The detected surface composition would then change until equilibrium has been reached between the amount of the preferentially sputtered species remaining at the surface and the fraction of these species "uncovered" by the ion beam. Since some preferential sputtering does take place during calcium-phosphate sputtering we believe that both processes are at work.

Figure 23:
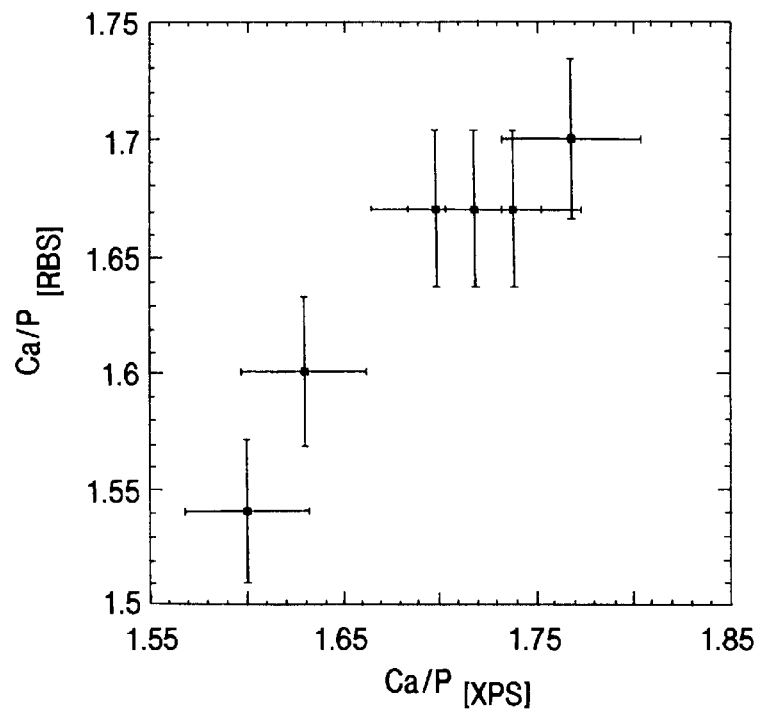

In FIG. 23 the Ca/P ratio has been plotted for a few coatings as obtained with RBS vs. the average bulk Ca/P ratio as determined from the ESCA by depth profiling. Two messages that we want to convey are: (i) some preferential sputtering does actually take place, and (ii) it is possible to obtain reliable quantitative composition of each coating from the sputter depth profile data.

Figure 24:
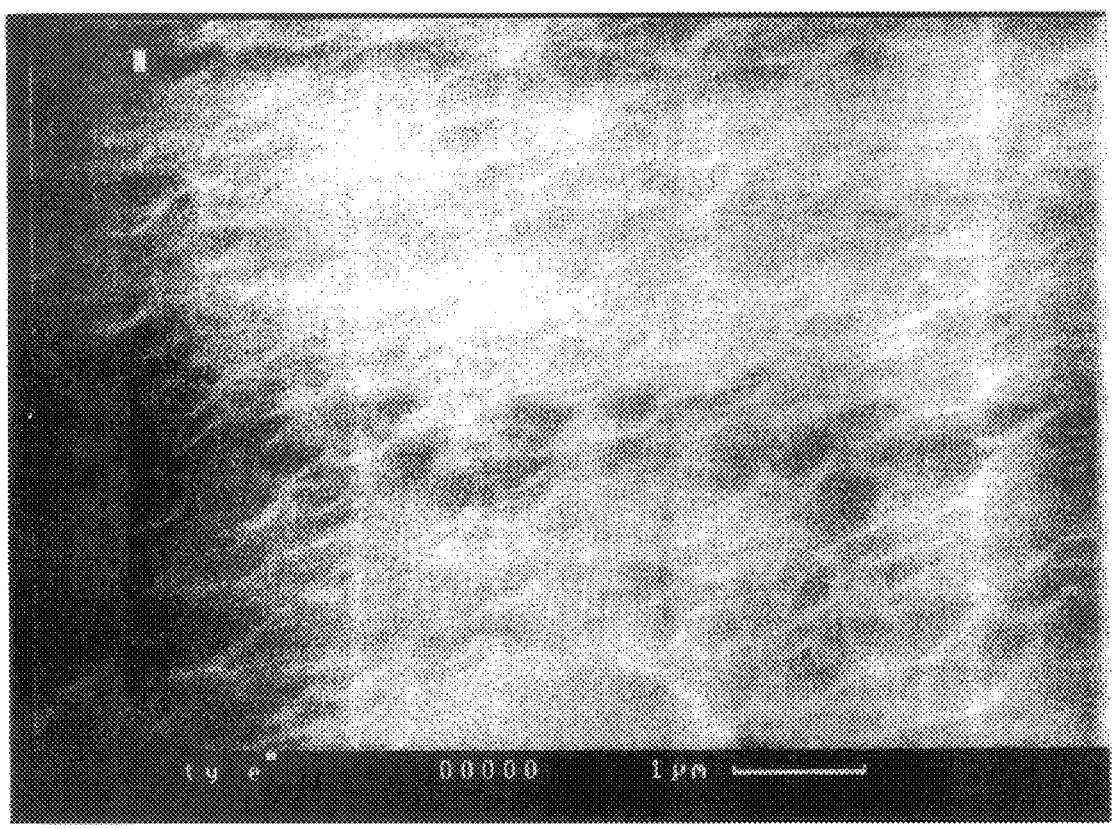
Figure 25:
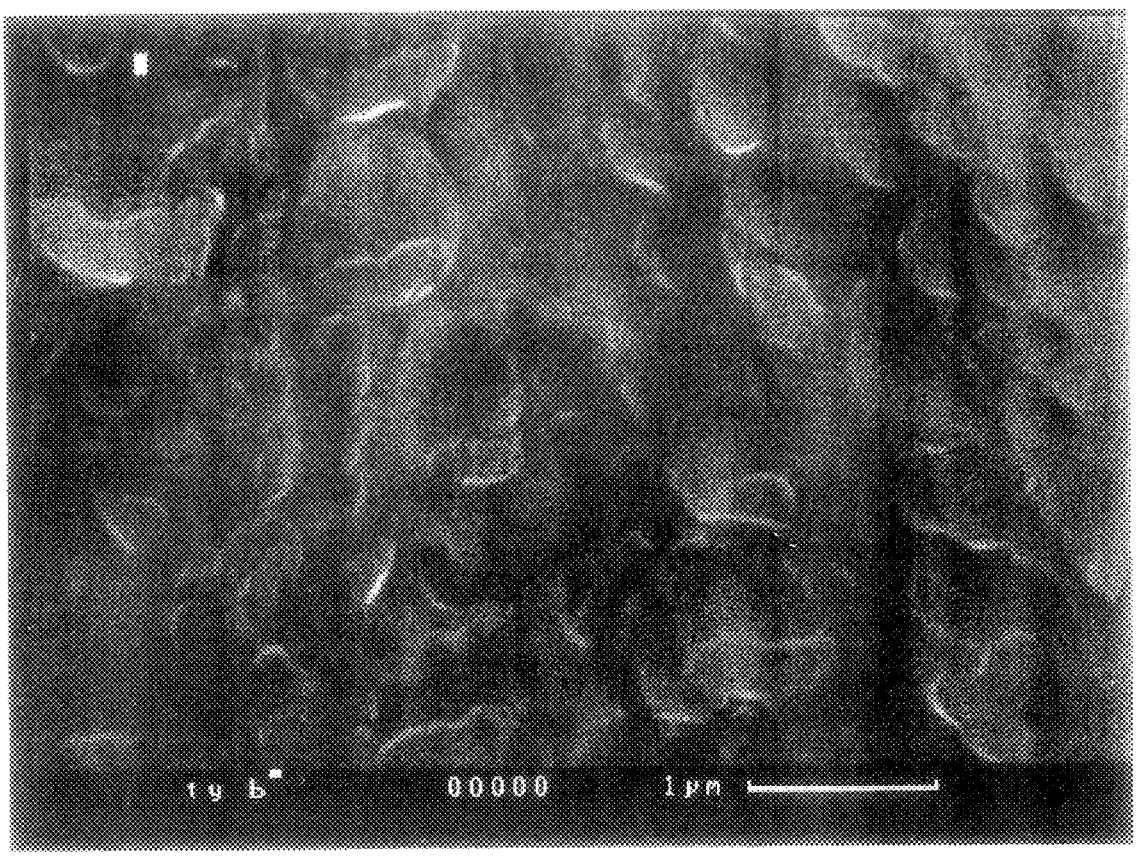

One of the aims with the present invention was to obtain smooth, well adherent coatings, without the disturbing features on a micrometer scale existing on the coatings prepared used laser ablation or plasma spraying. Moreover, we wanted to prepare coatings differing substantially with regard to dissolution velocity. It is well known that the dissolution of calcium-phosphate coatings depends strongly on a crystallinity of a coating, and on Ca/P ratio. Since we wanted to keep the Ca/P ratio constant, close to the stochiometric HA value, we decided to produce samples of different crystallinities. The crystallinity of our samples vs. after-treatment has been described in some detail in the XRD section above. This discussion can be summarized as follows: as deposited coatings were not fully amorphous, but heating in a flow of Ar saturated with water vapour increased the degree of crystallinity of the coatings substantially by increasing the size of crystallites as well as their density. This can be seen in electron micrograph (SEM) pictures taken from non heat treated as well as heat treated coatings as shown in FIGS. 24 and 25, respectively. FIG. 24 illustrates a non heat treated, 2 µm thick coating, while FIG. 25 illustrates a 2 µm thick coating heat treated for 13 h at 600° C. in the reactor described above. As can be seen no features attributable to microcrystallite grains can be detected for the non heat treated coatings, see FIG. 24, whereas heat treated coatings exhibit crystallite with typical grain sizes around 500 nm, see FIG. 25. It is also clear from the SEM pictures that the coatings do follow the morphology of the underlying substrates and that they are very smooth with no particle like features visible.

The magnification is approximately ×20000 for both pictures. Note the appearance of small crystallites on a heat treated sample. The non heat treated sample was so smooth that it was extremely difficult to obtain any contrast at these high magnifications.

To investigate the dissolution of our samples we have immersed the as prepared and heat treated samples, respectively, into a bovine serum solution for different time periods (2 days, 5 days and 7 days) and analyzed each sample using XPS and SEM. The XPS spectra of as deposited, i.e. non heat treated, samples immersed into bovine serum for 5 days indicated that the surface was "patchy". There were islands of calcium-phosphate film while other parts of the substrate surface were almost completely bare. The thickness of the remaining calcium-phosphate patches seemed to have decreased dramatically. The heat treated samples subjected to similar bovine serum exposure, on the other hand, showed a minor decrease of film thickness but the effect was too small to be quantifiable by sputter depth profiling.

Figure 26:
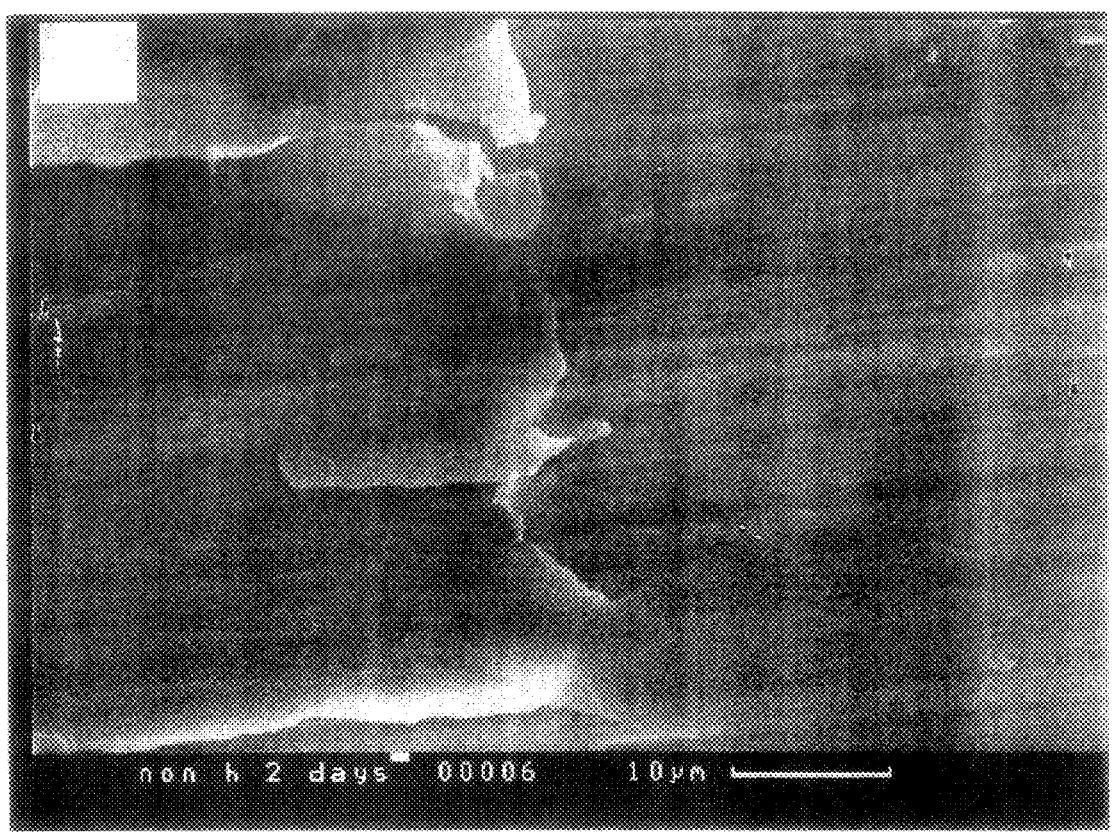
Figure 27:
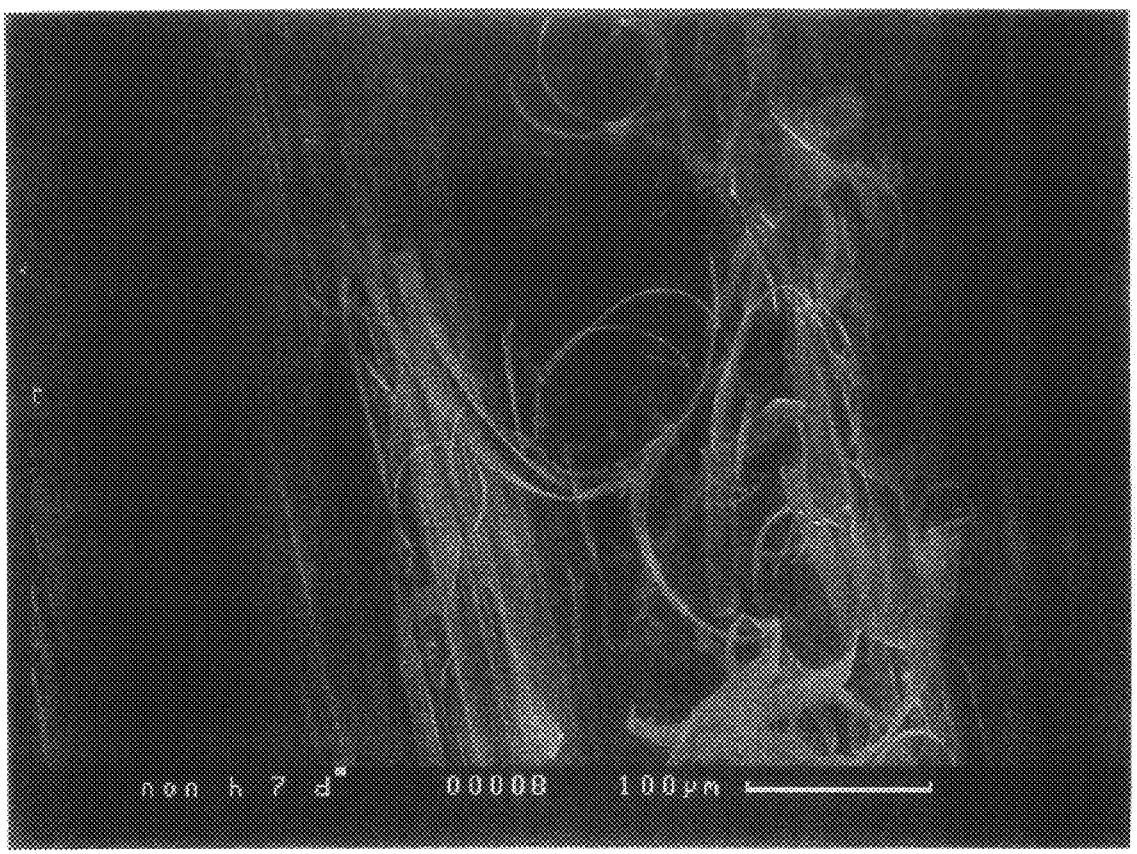

To further corroborate these results we have investigated the same samples exposed to bovine serum by SEM. The results for non-heat treated samples are shown in FIGS. 26 and 27 (for two days and seven days, respectively) while FIGS. 28, 29 and 30 show the SEM pictures of heat treated samples also kept in bovine serum for two days (FIGS. 28 and 29) and for seven days (FIG. 30).

After only two days in bovine serum the initially smooth and continuous non heat treated coating starts to dissolve. As can be seen in FIG. 26 the coating has partly dissolved from the surface already after two days. Note that the feature on the right hand side in FIG. 26 is the bare Ti-surface. The left hand side shows a "cracky" and smooth surface with featureless grains which is a remnant of the calcium-phosphate coating.

After seven days of exposure to bovine serum yarn-like, fluffy features which contained Ca and P (according to X-ray fluorescence analysis) appeared on a few spots. The "original" coating had disappeared, see FIG. 27.

Figure 28:
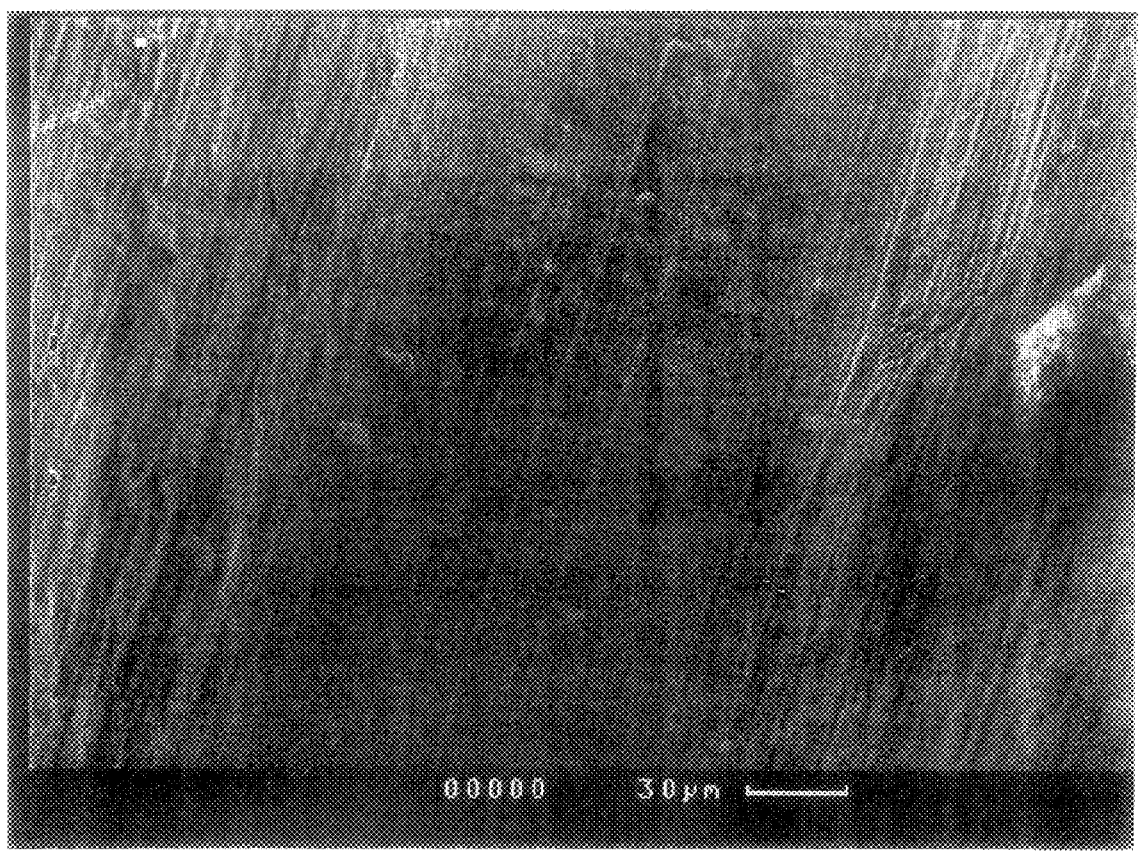
Figure 29:
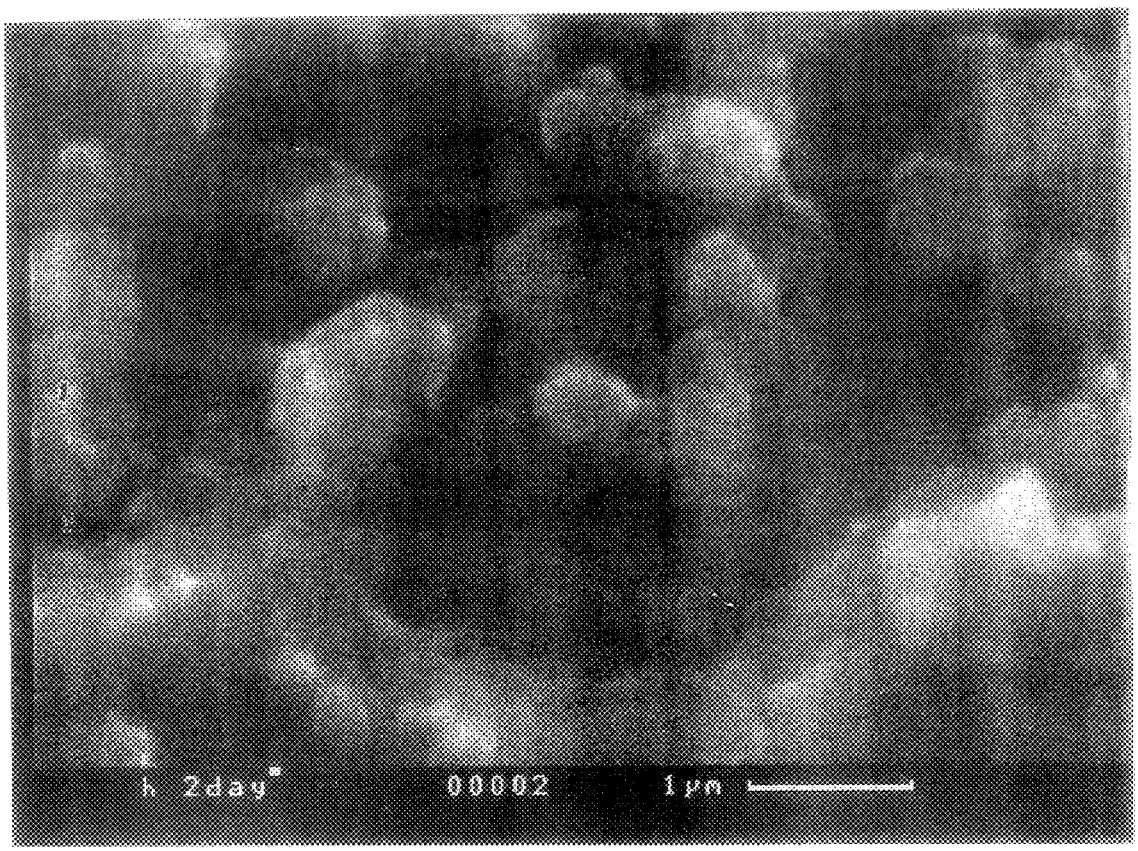
Figure 30:
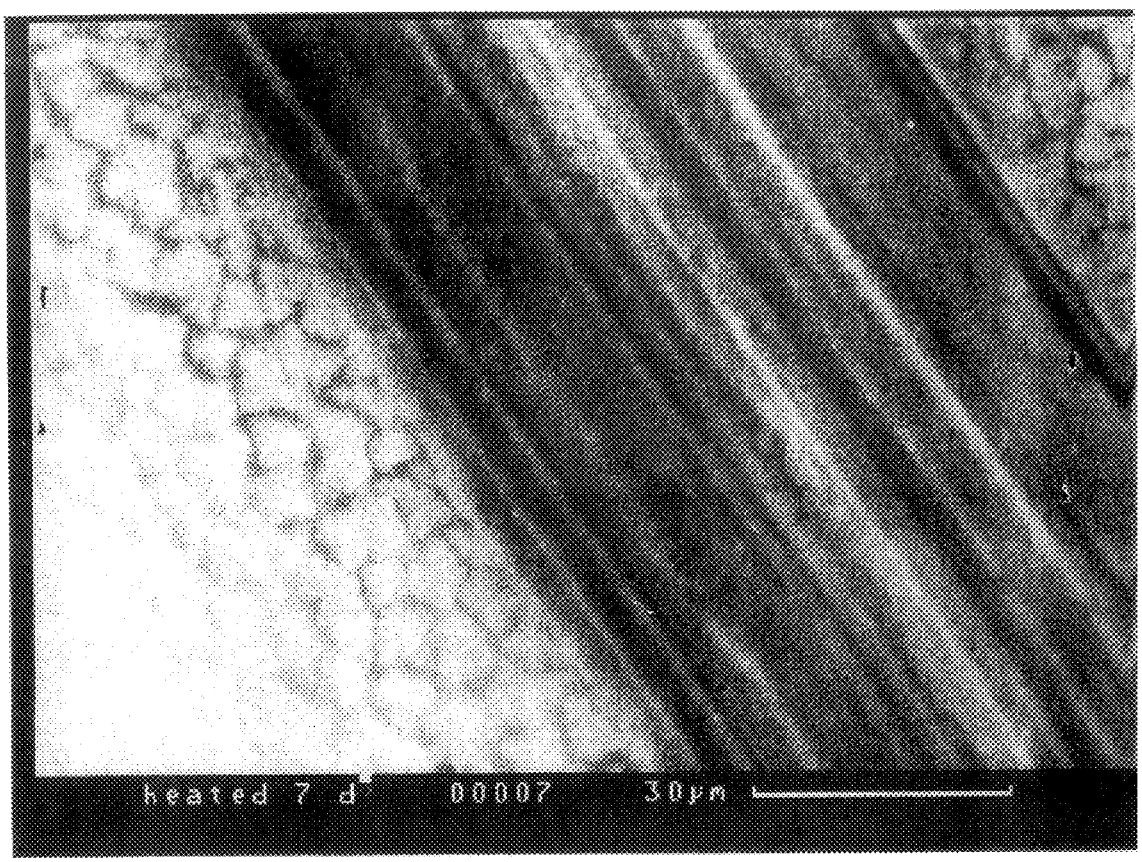

The SEM pictures of heat treated samples in FIGS. 28–30 show only minor differences between the unexposed samples and the samples exposed to bovine serum, respectively. The main difference was that we could detect dendrite-like features on top of the coating on a few parts of the samples exposed to bovine serum after 5 days (not shown). X-ray fluorescence analysis showed that such features mainly consisted of calcium and phosphorous. The features had developed into "humps" after 7 days of exposure to bovine serum as seen in a lower part of FIG. 30.

FIG. 29 shows a heat treated calcium-phosphate coated sample after 2 days in bovine serum. Note that there is almost no difference compared to the heat treated samples not exposed to bovine serum shown in FIG. 25 (the magnification is approximately ×17000, i.e. of the same order as the magnification of the corresponding SEM picture shown in FIG. 25).

FIG. 30 illustrates a heat treated sample after 7 days of exposure to bovine serum. Note that the whole surface is still covered by the calcium-phosphate coating.

Figure 7:
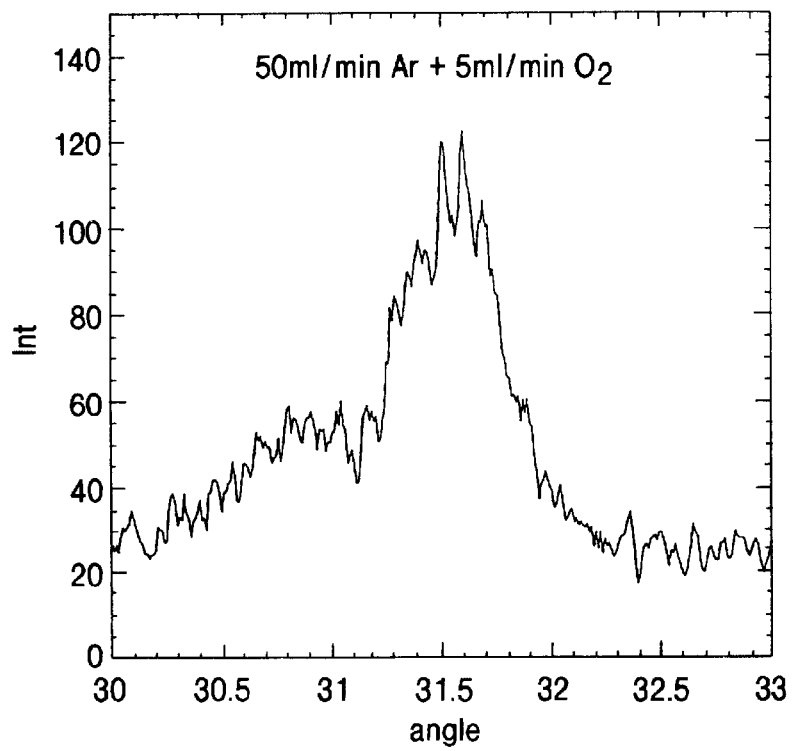
Figure 8:
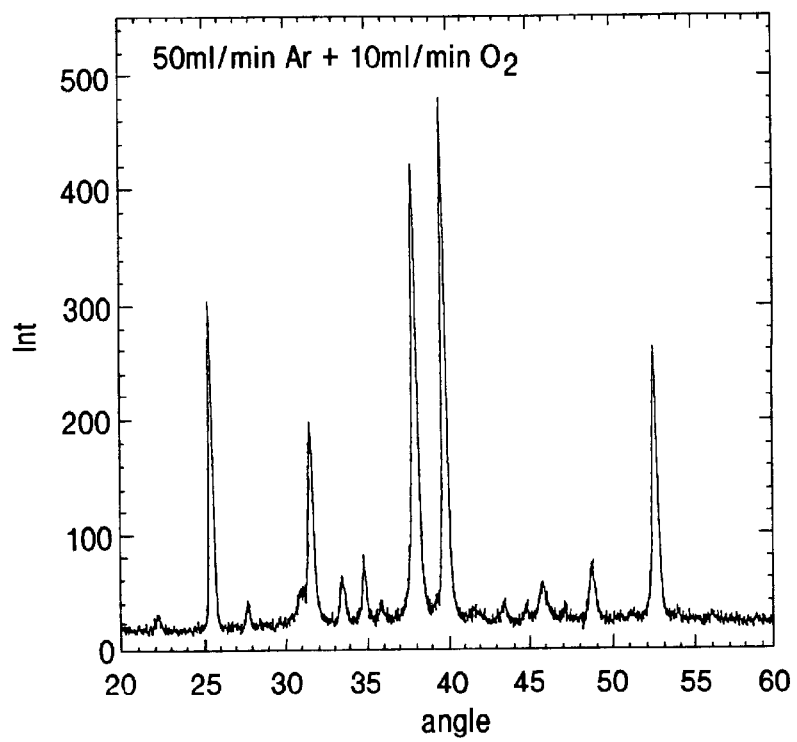
Figure 9:
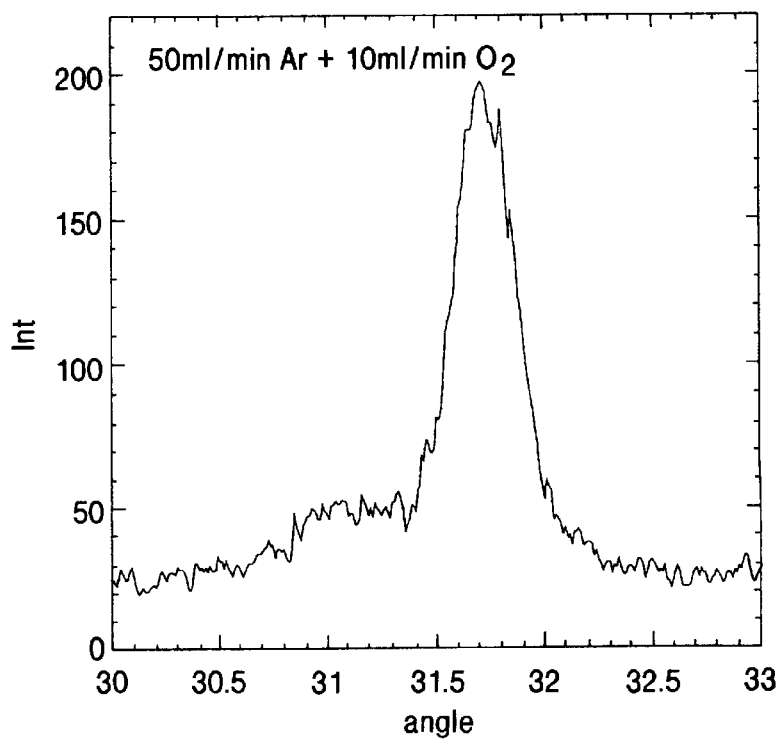
Figure 10:
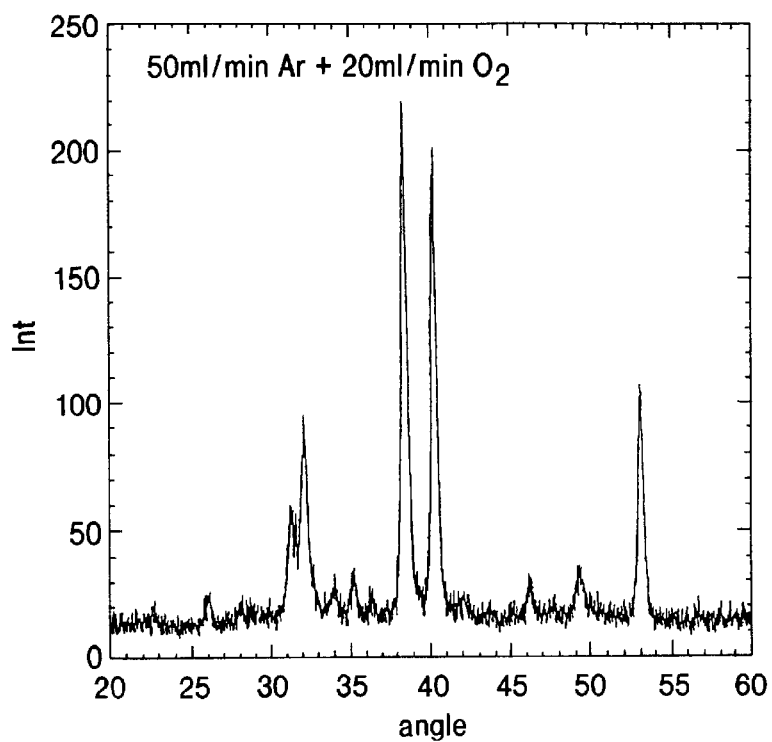
Figure 11:
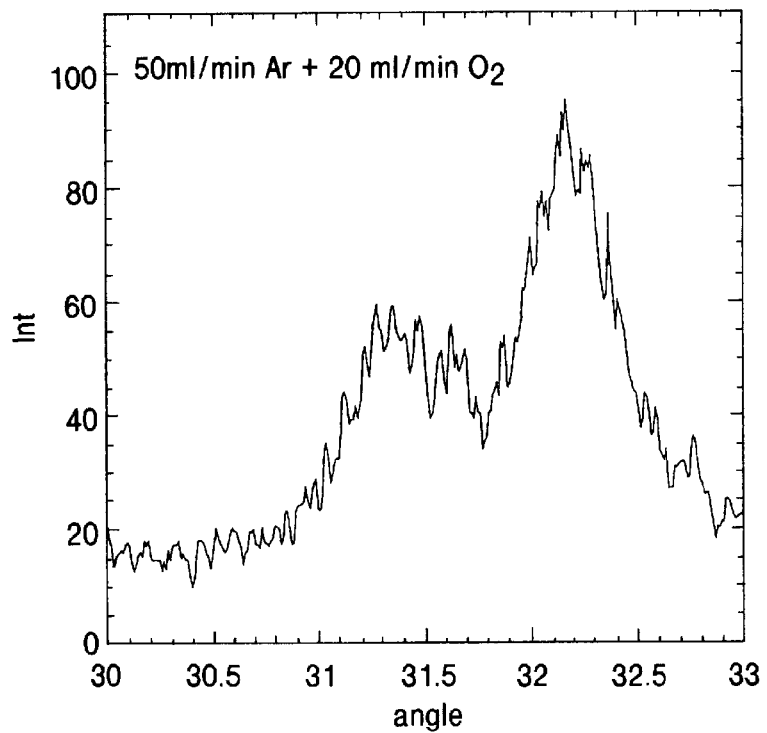
Figure 31:
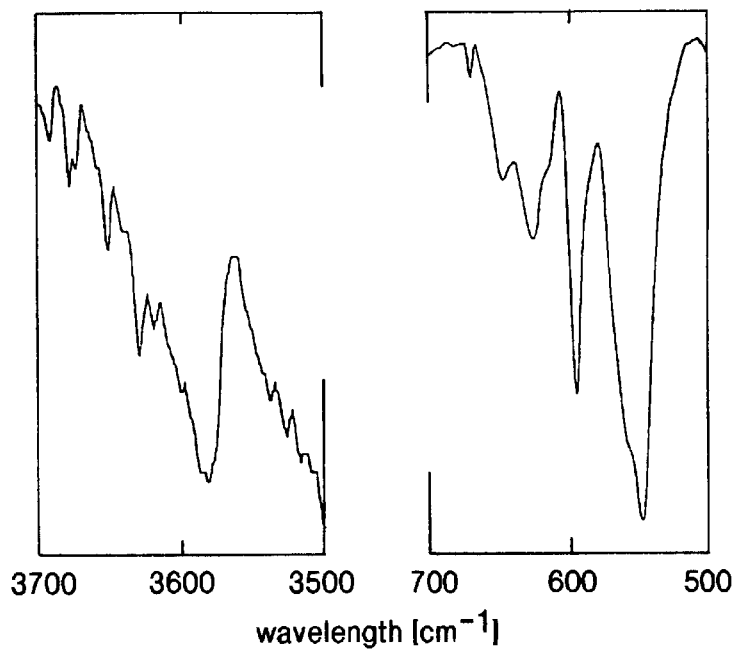
Figure 32:
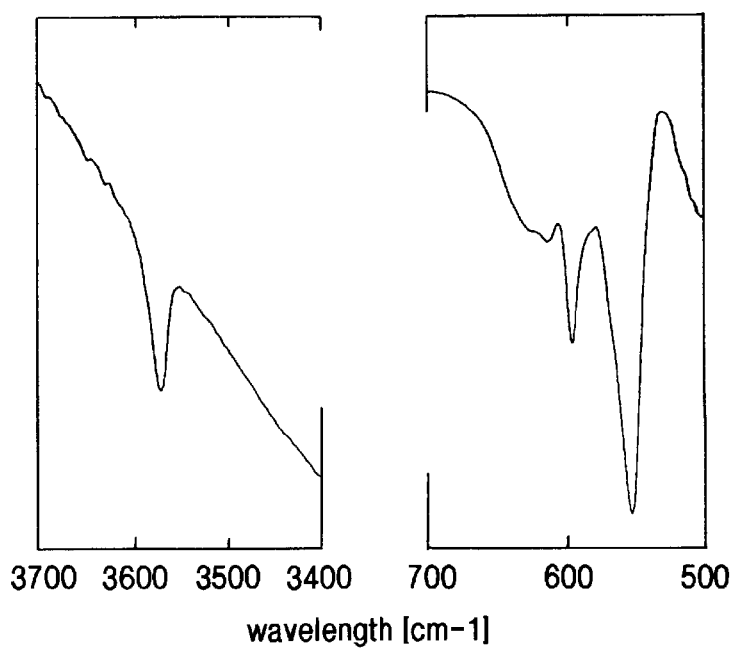

Finally, a characterization of the prepared calcium-phosphate coatings have been performed by means of Fourier Transform Infra Red Spectroscopy (FTIR) technique. The chemical component unique for hydroxyapatite compared with other calcium-phosphates is the OH-group. Other phosphates do contain hydrogen too, but as a chemically different specie. For example hydrogen in the dicalcium phosphate is not bonded to oxygen but constitutes rather a "chemical link" between the Ca and the $PO_4$ group. The FTIR technique enables one to detect many of the characteristic vibrations for a given compound, and in particular OH. It is not a quantitative technique and the amplitude of a particular OH-vibration cannot easily be compared between differently prepared samples having identical composition (for example the reflectivity, and thus the signal level will vary with surface roughness differently for different wave-lengths used in FTIR). Neither can the intensities of the same spectral feature of two identical samples obtained using two different equipments be compared with each other. Nevertheless it is useful to elucidate general trends, and compare features obtained using the same equipment not too far separated in wavelength. Here two FTIR spectra are presented: one of the non heat treated sample, FIG. 31, and another for the heat treated sample, FIG. 32. The spectrum in FIG. 31 was obtained in a vacuum pumped spectrometer superior in its performance (resolution signal/ noise ratio, etc.) to the other equipment used to collect data shown in FIG. 32, which operated in ambient. The right-hand side spectra of each figure correspond to the wave-length region where $PO_4$ vibrations are usually detected, while the left-hand side shows the region of the OH vibration. These results can be compared to the data available in the literature, particularly with the data of P. Ducheyne, W. van Raedmonck, J. C. Heughebaert and M. Heughebaert, Biomaterials, 7(1986) p.97, mentioned earlier. In FIG. 7 of the Ducheyne et al article the authors analyze the FTIR spectra of various calcium phosphates. From the comparison of our spectra in FIGS. 31 and 32 with their results we can conclude that our coating consist to a large extent of the defect-free hydroxyapatite.

The examples above indicate that it is possible to produce thin CaP coatings with well defined chemical properties close to stochiometric HA. We have shown that such coatings have well controlled crystallographic properties, which can be varied within the range from nearly amorphous to nearly fully crystallized with the heat treatment method described. The in-vivo degradation of such coatings can be well controlled, since the dissolution rate depends strongly on the degree of crystallinity. Thus, the underlying long-term clinically well documented surface will be exposed after the coating has dissolved during the initial healing phase. Pre-clinical in-vivo data indicate that such coatings may have a substantial effect on the interaction process between the coating and the surrounding tissue. The biological verification of the hypothesis that a combination of a thin calcium-phosphate coating and an underlying clinically well-documented surface with micro-pitted topography would promote a significantly higher bone-implant contact than a non-coated surface was evident in a series of studies in rabbits. The animals were followed for six weeks. In both cortical and trabecular bone it was found that mineralized bone was in greater contact with the implant surfaces with a less than 2 micron thick calcium-phosphate coating than with the non-coated titanium surface.

In vitro data indicates that the coating is resorbable and has a predetermined dissolution rate. This makes it possible to predict for a coated implant element a specific time period under which the coating is active. After that time period the coating has been disappeared and the underlying surface is exposed.

Therefore it is possible to vary the implant element according to the indicated technical parameters and provide time-programmed surfaces. The biological effects of calcium-phosphate/titanium-oxide programmed surfaces is indicated by the present biological results where differences in bone formation distant to the implant surface, (but within threads), may be modulated depending on the crystallinity of the calcium-phosphate coating.

The invention is not limited to the specific methods and embodiments that has been illustrated so far but can be varied within the scope of the accompanying claims.

What is claimed is:

1. An implant element for permanent anchorage in bone tissue comprising:
    at least a bio-compatible, osseointegrative, tissue-facing surface; and
    a thin, conformal, adherent calcium-phosphate coating applied to said surface; wherein said coating has a pre-determined rate of dissolution controlled by a crystal structure imparted by a controlled anneal step.

2. An implant element according to claim 1, wherein said coating has a thickness of from about 0.1 micrometer to about 3 micrometers.

3. An implant element according to claim 1, wherein said coating has a thickness of from about 0.1 micrometer to about 10 micrometers.

4. An implant element according to claim 1, wherein said osseointegrative surface is a titanium surface having micro-pits in the range from about 0.01 micrometers to about 1 micrometer.

5. An implant element according to claim 1, wherein said calcium-phosphate coating has a controlled stoichiometry which can be varied from about 1.47 to about 2.86 Ca/P.

6. An implant element according to claim 1, wherein said stoichiometry is substantially the same as the stoichiometry of hydroxyapatite.

7. A method for providing a thin, conformal, adherent calcium-phosphate coating on an implant element for permanent anchorage in bone tissue, the method comprising the steps of:
    providing a radio-frequency sputtering chamber comprising:
        independent, regulated supplies of argon, oxygen, and hydrogen gas, connected to said chamber,
        electrically-isolated mounting means for said implant element within said chamber,
        means of rotating said mounting means,
        a source of calcium-phosphate within said chamber, and
        a source of radio-frequency radiation within said chamber;
    mounting at least one implant element comprising a bio-compatible, osseointegrative, tissue-facing surface on said mounting means;
    flowing a deposition gas within said chamber;
    depositing a film of calcium-phosphate, from said calcium-phosphate source, onto said osseointegrative surface;
    providing an annealing reactor comprising:
        a chamber,
        a heat source thermally connected to said chamber,
        a gas humidifier connected to said chamber,
        a source of argon gas connected to said humidifier, and
        a source of water connected to said humidifier;
    placing at least one coated implant element within said reactor;
    flowing water-saturated argon gas through said reactor; and
    heating said coated implant element.

* * * * *